US009249455B2

(12) United States Patent
Moser et al.

(10) Patent No.: US 9,249,455 B2
(45) Date of Patent: Feb. 2, 2016

(54) METHODS FOR DETECTION AND QUANTIFICATION OF SMALL RNA

(75) Inventors: Michael J. Moser, Madison, WI (US); Vecheslav A. Elagin, Waunakee, WI (US)

(73) Assignee: LUMINEX CORPORATION, Austin, TX (US)

( * ) Notice: Subject to any disclaimer, the term of this patent is extended or adjusted under 35 U.S.C. 154(b) by 1667 days.

(21) Appl. No.: 12/425,088

(22) Filed: Apr. 16, 2009

(65) Prior Publication Data
US 2009/0275039 A1 Nov. 5, 2009

Related U.S. Application Data

(60) Provisional application No. 61/046,162, filed on Apr. 18, 2008.

(51) Int. Cl.
*C12Q 1/68* (2006.01)
(52) U.S. Cl.
CPC ............ *C12Q 1/6844* (2013.01); *C12Q 1/6818* (2013.01)
(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 4,996,143 A | 2/1991 | Heller et al. |
| 5,210,015 A | 5/1993 | Gelfand et al. |
| 5,432,272 A | 7/1995 | Benner |
| 5,604,097 A | 2/1997 | Brenner |
| 5,843,669 A | 12/1998 | Kaiser et al. |
| 5,846,717 A | 12/1998 | Brow et al. |
| 5,928,869 A | 7/1999 | Nadeau et al. |
| 5,965,364 A | 10/1999 | Benner |
| 6,001,983 A | 12/1999 | Benner |
| 6,007,984 A | 12/1999 | Wang et al. |
| 6,037,120 A | 3/2000 | Benner |
| 6,140,496 A | 10/2000 | Benner |
| 6,232,462 B1 | 5/2001 | Collins et al. |
| 6,548,250 B1 | 4/2003 | Sorge |
| 6,833,257 B2 | 12/2004 | Lee et al. |
| 6,977,161 B2 | 12/2005 | Grenier et al. |
| 7,422,850 B2 | 9/2008 | Marshall et al. |
| 7,517,651 B2 | 4/2009 | Marshall et al. |
| 7,541,147 B2 | 6/2009 | Marshall et al. |

OTHER PUBLICATIONS

Raymond et al. (RNA, 2005, 11:1737-1744).*
Chen et al. (Nucleic Acids Research, 2005, 33(20):e179, p. 1-9).*
Johnson et al. (Nucleic Acids Research, 2004, 32(6):1937-1941).*
Johnson et al., "A third base pair for the polymerase chain reaction: inserting isoC and isoG", *Nucleic Acids Research*, vol. 32, No. 6, 2004, (pp. 1937-1941).
Jurczyk et al., "Synthesis of 2'-Deoxyisoguanosine 5'-Triphosphate and 2'-Deoxy-5- methylisocytidine 5'-Triphosphate", *Helvetica Chimica Acta*, vol. 82, 1999 (pp. 1005-1015).
Livak, et al., "Oligonucleotides with Fluorescent Dyes at Opposite Ends Provide a Quenched Probe System Useful for Detecting PCR Product and Nucleic Acid Hybridization," *PCR Methods and Applications* (4) No. 6, pp. 357-362, 1995. U.S.
Lutz, Michael J. et al., "Differential discrimination of DNA polymerases for variants of the non-standard nucleobase pair between xanthosine and 2,4-diaminopyrimidine, two components of an expanded genetic alphabet", *Nucleic Acids Research*, vol. 24, No. 7, 1996 (pp. 1308-1313).
McMinn et al., "Efforts toward Expansion of the Genetic Alphabet: DNA Polymerase Recognition of a Highly Stable, Self-Pairing Hydrophobic Base", *J. Am. Chem. Soc.*, vol. 121, No. 49, 1999.(pp. 11585-11586).
Moser et al., "Quantifying Mixed Populations of Drug-Resistant Human Immunodeficiency Virus type 1", *Antimicrobial Agents and Chemotherapy*, vol. 49, No. 8, Aug. 2005 (pp. 3334-3340).
Moser et al., "Enzymatic repair of an expanded genetic information system", *Nucleic Acids Research*, vol. 31, No. 27, 2003 (pp. 5048-5053).
Newton et al., "The production of PCR products with 5' single-stranded tails using primers that incorporate novel phosphoramidite intermediates", *Nucleic Acids Research*, vol. 21, No. 5, 1993 (pp. 1155-1162).
Piccirilli et al., "Enzymatic incorporation of a new base pair into DNA and RNA extends the genetic alphabet", Reprinted from *Nature*, vol. 343, No. 6253, Jan. 4, 1990 (pp. 33-37).
Sherrill, C.B. et al., "Nucleic acid analysis using an expanded genetic alphabet to quench fluorescence." *Journal of the American Chemical Society*, vol. 126, No. 14, pp. 4550-4556, XP002314862, Apr. 14, 2004.
Sismour et al., "PCR amplification of DNA containing non-standard base pairs by variants of reverse transcriptase from Human Immunodeficiency Virus-1", *Nucleic Acids Research*, vol. 32, No. 2, 2004.(pp. 728-735).
Switzer et al., "Enzymatic Recognition of the Base Pair between Isocytidine and Isoguanosine", *Biochemistry*, vol. 32, No. 39, 1993 (pp. 10489-10496).
Tor et al., "Site-Specific Enzymatic Incorporation of an Unnatural Base, $N^6$-(6-Aminohexyl)isoguanosine, into RNA", *J. Am. Chem. Soc.*, vol. 115, No. 11, 1993 (pp. 4461-4467).
Whitcombe, et al. "Detection of PCR Products Using Self-Probing Amplicons and Fluorescence," *Nature Biotech*, (17) No. 8, pp. 804-807, 1999. Nature Publishing, U.S.
Zubay, "A Case for an Additional RNA Base Pair in Early Evolution", Reprint from: *The Roots of Modern Biochemistry*, © 1988 Walter de Gruyter & Co., Berlin, New York (4 pp.).

* cited by examiner

*Primary Examiner* — Stephanie K Mummert
(74) *Attorney, Agent, or Firm* — Parker Highlander PLLC

(57) ABSTRACT

Disclosed are methods, kits, and components for detecting small RNA molecules, such as microRNA and siRNA, in a sample. The methods utilize primers and reporter molecules comprising non-natural bases. The disclosed kits may include one or more components for performing the disclosed methods.

19 Claims, 7 Drawing Sheets

SEQUENCE LISTING

<160> NUMBER OF SEQ ID NOS: 55

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic

```
                                     -continued
        primer

<400> SEQUENCE: 1
ugagguagua gguuguauag uu                                              22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 2
ugagguagua gguuguaugg uu                                              22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 3
ugagguagua gauuguauag uu                                              22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 4
ugagguagua guuuguacag u                                               21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtgtccatga ggtagtag                                                   18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 6
ngtgtccatg aggtagtag                                                  19

<210> SEQ ID NO 7
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 7
ngtgtccatg aggtagtag                                                  19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 8
ncgtgtccat gaggtagtag                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 9
ngcacaggtt gaggtagtag                                                 20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtgtccatga ggtagtagg                                                  19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 11
ngtgtccatg aggtagtagg                                                 20

<210> SEQ ID NO 12
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 12
ngtgtccatg aggtagtagg                                                     20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 13
ncgtgtccat gaggtagtag g                                                   21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 14
ngcacaggtt gaggtagtag g                                                   21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtgtccatga ggtagtaga                                                      19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 16
ngtgtccatg aggtagtaga                                                     20
```

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 17
ngtgtccatg aggtagtaga                                                    20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 18
ncgtgtccat gaggtagtag a                                                  21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 19
ngcacaggtt gaggtagtag a                                                  21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgtccatga ggtagtagt                                                     19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 21
```

```
ngtgtccatg aggtagtagt                                                    20
```

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 22

```
ncgtgtccat gaggtagtag t                                                  21
```

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 23

```
ngcacaggtt gaggtagtag t                                                  21
```

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 24

```
nggcagacag gacaactata c                                                  21
```

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 25

```
nggcagacag gacaactata c                                                  21
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<221> NAME/KEY: modified_base
<222> LOCATION: (1)..(1)
<223> OTHER INFORMATION: d-iC

<400> SEQUENCE: 26
nggcagacag gacaactata                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 27
nggcagacag gacaactata                                              20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 28
nccgtctgtc cagaactata c                                            21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 29
nccgtctgtc cagaactata c                                            21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgtctgtcc agaactatac a                                            21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
              primer

<400> SEQUENCE: 31
ccgtctgtcc agaactatac                                                    20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgtctgtcc agaactata                                                     19

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccgtctgtcc agaactat                                                      18

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccgtctgtcc agaaccacac                                                    20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccgtctgtcc agaaccacac a                                                  21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccgtctgtcc agaaccacac aa                                                 22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (1)..(1)
<223> OTHER INFORMATION: d-iC

<400> SEQUENCE: 37
nggcagacag gacaaccata c                                         21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 38
nggcagacag gacaaccata c                                         21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccgtctgtcc agaaccatac a                                         21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 40
nccgtctgtc cagaaccata c                                         21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: d-iC

<400> SEQUENCE: 41
nccgtctgtc cagaaccata c                                         21

<210> SEQ ID NO 42
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 42
ccgtctgtcc agaaccatac                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccgtctgtcc agactatgca                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccgtctgtcc agactgtaca                                                    20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccgtctgtcc agactgtaca a                                                  21

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccgtctgtcc agacagcac                                                     19

<210> SEQ ID NO 47
<211> LENGTH: 22
<212> TYPE: RNA
<213> ORGANISM: Homo sapiens

<400> SEQUENCE: 47
ugagguagua gguuguauag uu                                                 22

<210> SEQ ID NO 48
<211> LENGTH: 22
<212> TYPE: RNA
<213> ORGANISM: Homo sapiens

<400> SEQUENCE: 48
ugagguagua gguugugugg uu                                                 22
```

```
<210> SEQ ID NO 49
<211> LENGTH: 22
<212> TYPE: RNA
<213> ORGANISM: Homo sapiens

<400> SEQUENCE: 49
ugagguagua gguuguaugg uu                                              22

<210> SEQ ID NO 50
<211> LENGTH: 22
<212> TYPE: RNA
<213> ORGANISM: Homo sapiens

<400> SEQUENCE: 50
ugagguagua gauuguauag uu                                              22

<210> SEQ ID NO 51
<211> LENGTH: 21
<212> TYPE: RNA
<213> ORGANISM: Homo sapiens

<400> SEQUENCE: 51
agagguagua gguugcauag u                                               21

<210> SEQ ID NO 52
<211> LENGTH: 21
<212> TYPE: RNA
<213> ORGANISM: Homo sapiens

<400> SEQUENCE: 52
ugagguagga gguuguauag u                                               21

<210> SEQ ID NO 53
<211> LENGTH: 21
<212> TYPE: RNA
<213> ORGANISM: Homo sapiens

<400> SEQUENCE: 53
ugagguagua guuguacag u                                                21

<210> SEQ ID NO 54
<211> LENGTH: 21
<212> TYPE: RNA
<213> ORGANISM: Homo sapiens

<400> SEQUENCE: 54
ugagguagua guuugugcug u                                               21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccgtctgtcc agattgtaca a                                               21
```

US 9,249,455 B2

METHODS FOR DETECTION AND QUANTIFICATION OF SMALL RNA

CROSS-REFERENCE TO RELATED APPLICATIONS

This application claims priority to U.S. Provisional Application No. 61/046,162, filed Apr. 18, 2008, the entire contents of which are hereby incorporated by reference in its entirety.

TECHNICAL FIELD

The present methods and kits relate broadly to the identification of nucleic acids using nucleic acid amplification techniques. In particular, the methods and kits relate to methods of detecting and quantifying small RNA molecules, such as microRNA.

BACKGROUND

MicroRNA (miRNA) are small RNA molecules that are expressed as pol II transcripts in eukaryotic organisms. These molecules have been shown to regulate gene expression, mRNA splicing, and histone formation. They also have been shown to have tissue-specific and developmental-specific expression patterns. Thus, these small RNA molecules are of interest in the elucidation of biological processes, disease states, and development.

SUMMARY

There are provided herein methods and kits for quickly, easily and inexpensively detecting and quantifying small RNA in a biological sample. The methods described herein provide a homogenous, probe-free assay for the detection of a variety of small RNAs, including miRNA and siRNA.

In one aspect, the invention provides a method comprising: (a) contacting a sample to be tested for the presence or absence of a target small RNA with: (i) a first primer comprising a target binding region and a tail region, wherein the target binding region comprises about 12 or fewer nucleotides that are complementary to the small RNA; (ii) a second primer comprising a target binding region and a tail region, wherein the target binding region comprises about 12 or fewer nucleotides that are complementary to the reverse complement of the small RNA, wherein the tail regions of the first primer, the second primer, or both the first primer and the second primer comprise a first label and a first non-natural base; (b) extending the first primer under conditions suitable to produce a first reaction product of the small RNA, if present in the sample; (c) amplifying the first reaction product with the first primer and the second primer under conditions suitable to produce an amplification product, wherein a second non-natural base conjugated to a second label is incorporated into the amplification product opposite the first non-natural base, and wherein the first non-natural base is iso-C or iso-G and the second non-natural base is the other of iso-C or iso-G; and (d) detecting the amplification products produced in step (c) by observing a signal from the first label, the second label, or both the first label and the second label.

In some embodiments, the target small RNA is from about 16 to about 30 nucleotides in length, or from about 19 to about 24 nucleotides in length, or from about 21 to about 23 nucleotides in length.

Each of the first primer and the second primer may comprise a target binding region and a tail region. In some embodiments, the target binding regions of the first primer and/or the second primer comprise from about 7 to about 10 nucleotides. Likewise, the tail regions of the first primer and/or the second primer each comprise from about 10 to about 25 nucleotides, or from about 7 to about 15 nucleotides. The tail region of the first primer, the second primer, or both may comprise one or more non-natural bases.

The non-natural bases used in the methods described herein may be selected from iso-C and iso-G. In suitable embodiments, the first non-natural base is iso-C and the second non-natural base is iso-G. For example, the reporter may comprise an nucleotide triphosphate of iso-G conjugated to a label, such as a quencher.

The extension of the first primer is under conditions suitable to produce a first reaction product of the small RNA. Typically, these conditions allow for the specific hybridization of the target binding region of the first primer to the target small RNA. In some embodiments, the step of annealing and extension to produce a first reaction product is performed at temperature from about 15° C. to about 50° C.

The step of amplifying the first reaction product with the first primer and the second primer is under conditions suitable to produce an amplification product. In the first round of amplification, these conditions allow for the specific hybridization of the target binding region of the second primer to the first amplification product. In some embodiments, this annealing step is performed at a temperature from about 35° C. to about 45° C. Subsequent annealing steps may be performed at a temperature at least about 55° C.

The primers described herein may be designed to have varying specificity for related small RNA isoforms. In some embodiments, the primers are capable of discriminating between related isoforms. In other embodiments, the primers are not capable of discriminating between related isoforms. Therefore, in some methods, the first primer, the second primer, or both are specific for a single small RNA isoform. For example, the single small RNA isoform differs from other isoforms at one or more specific nucleotide positions, and at least the 4 terminal nucleotides at the 3' end of first primer, the second primer, or both are complementary to the single isoform, but not complementary to the other isoforms.

In some embodiments, one or both of the first primer and the second primer comprise a first label. In suitable embodiments, the first label is a fluorophore. The first label may interact with the second label, i.e., the first label and the second label may form an interactive dye-quencher pair. In such embodiments, the first label is a fluorophore and the second label is a quencher. For example, the fluorophore may be FAM or HEX and the quencher may be Dabcyl.

In some embodiments, the methods may be used to quantitate the amount of target small RNA in a sample. In such embodiments, the step of detecting comprises quantifying the amount of the small RNA in the sample. The step of quantifying may comprise correlating the amount of signal observed from the first label, the second label or both the first label and the second label, to the amount of small RNA in the sample. In other embodiments, the step of detecting comprises measuring the signal from the first label, the second label, or both during the amplification. Alternatively, the step of detecting may comprise determining the melting temperature of the amplification products.

The methods described herein may be used to detect and quantify a wide variety of small RNAs. In particular embodiments, the small RNA is a miRNA, e.g., a miRNA selected from the group consisting of: miR-1, miR-7, miR-9*, miR-10a, miR-10b, miR-15a, miR-15b, miR-16, miR-17-3p, miR-17-5p, miR-18, miR-19a, miR-19b, miR-20, miR-21, miR-22, miR-23a, miR-23b, miR-24, miR-25, miR-26a, miR-26b, miR-27a, miR-28, miR-29a, miR -29b, miR-29c, miR-30a-5p, miR-30b, miR-30c, cmiR-34c, miR-92, miR-93, miR-95, miR -96, miR-98, miR-99a, miR-99b, miR-100, miR-101, miR-103, miR-105, miR-106a, miR -107, miR-122, miR-122a, miR-124, miR-124, miR-124a, miR-125a, miR-125b, miR-126, miR-126*, miR-127, miR-128a, miR-128b, miR-129, miR-130a, miR-130b, miR-132, miR -133a, miR-133b, miR-134, miR-135a, miR-135b, miR-136, miR-137, miR-138, miR-139, miR-140, miR-141, miR-142-3p, miR-143, miR-144, miR-145, miR-146, miR-147, miR -148a, miR-148b, miR-149, miR-150, miR-151, miR-152, miR-153, miR-154*, miR-154, miR-155, miR-181a, miR-181b, miR-181c, miR-182*, miR-182, miR-183, miR-184, miR -185, miR-186, miR-187, miR-188, miR-189, miR-190, miR-191, miR-192, miR-193, miR -194, miR-195, miR-196a, miR-196b, miR-197, miR-198, miR-199a*, miR-199a, miR-199b, miR-200a, miR-200b, miR-200c, miR-202, miR-203, miR-204, miR-205, miR-206, miR -208, miR-210, miR-211, miR-212, miR-213, miR-213, miR-214, miR-215, miR-216, miR -217, miR-218, miR-220, miR-221, miR-222, miR-223, miR-224, miR-296, miR-299, miR -301, miR-302a*, miR-302a, miR-302b*, miR-302b, miR-302d, miR-302c*, miR-302c, miR -320, miR-323, miR-324-3p, miR-324-5p, miR-325, miR-326, miR-328, miR-330, miR-331, miR-337, miR-338, miR-339, miR-340, miR-342, miR-345, miR-346, miR-363, miR-367, miR-368, miR-370, miR-371, miR-372, miR-373*, miR-373, miR-374, miR-375, miR-376b, miR-378, miR-379, miR-380-5p, miR-380-3p, miR-381, miR-382, miR-383, miR-410, miR -412, miR-422a, miR-422b, miR-423, miR-424, miR-425, miR-429, miR-431, miR-448, miR -449, miR-450, miR-451, let7a, let7b, let7c, let7d, let7e, let7f, let7g, let71, miR-376a, and miR-377.

In another aspect, the invention provides a method for simultaneously detecting two or more target small RNA isoforms. In one embodiment, the method comprises: (a) contacting a sample to be tested for the presence or absence of at least two target small RNA isoforms with: (i) a first primer comprising a target binding region and a tail region, wherein the target binding region comprises about 12 or fewer nucleotides that are complementary to at least two small RNA isoforms; (ii) a second primer comprising a target binding region and a tail region, wherein the target binding region comprises about 12 or fewer nucleotides that are complementary to the reverse complement of a first small RNA isoform, and the tail region comprises a first label and a first non-natural base; (iii) a third primer comprising a target binding region and a tail region, wherein the target binding region comprises about 12 or fewer nucleotides that are complementary to the reverse complement of a second small RNA isoform, and the tail region comprises a second label and a second occurrence of the first non-natural base; (b) extending the first primer under conditions suitable to produce a first reaction product of the at least two small RNA isoforms, if present in the sample; (c) amplifying the first reaction product, with the first primer, the second primer, and the third primer under conditions suitable to produce amplification products of the first small RNA isoform and the second small RNA isoform, wherein a second non-natural base comprising a third label is incorporated into the amplification products opposite the first non-natural base and wherein the first non-natural base is iso-C or iso-G, and the second non-natural base is the other of iso-C or iso-G; and (d) detecting the amplification products produced in step (c) by observing a signal from the first label, the second label, or both the first label and the second label, thereby determining the presence or absence of the target small RNA isoforms in the sample.

In some embodiments, a plurality of labels (e.g., fluorophores) is used to detect the two or more target small RNA isoforms. For example, the first label may comprise a first fluorophore and the second label may comprise a second fluorophore. Each specific primer may include an identical non-natural nucleotide base and a label (e.g., a fluorescent label). Each of the at least two labels may be different from the other. For example, one label may be fluorescein (FAM) and the other label may be hexachlorofluorescein (HEX). For example, the first fluorophore may be one of FAM or HEX and the second fluorophore may be the other of FAM or HEX. In some embodiments, the third label may comprise a quencher, e.g., Dabcyl.

In some embodiments, the signal one or more labels is observed during the amplification. In a particular embodiment, the labels comprise a dye-quencher pair. In this embodiment, a signal from a first label decreases during the reaction when the first small RNA isoform is present in the sample and a signal from a second label decreases during the reaction when the second small RNA isoform is present in the sample. In some embodiments, the step of detecting the amplification products comprises measuring the amount of signal from the first label, the second label, or both during the amplification thereby quantifying the relative amount of first small RNA isoform and the second small RNA isoform in the sample. In other embodiments, the methods may further comprise the step of determining the melting temperature of the amplification product of the first small RNA isoform and the second small RNA isoform in the sample, if present, wherein the signal from the first label, the second label, or both, increases upon melting of the amplification products.

DETAILED DESCRIPTION

Figure 1:
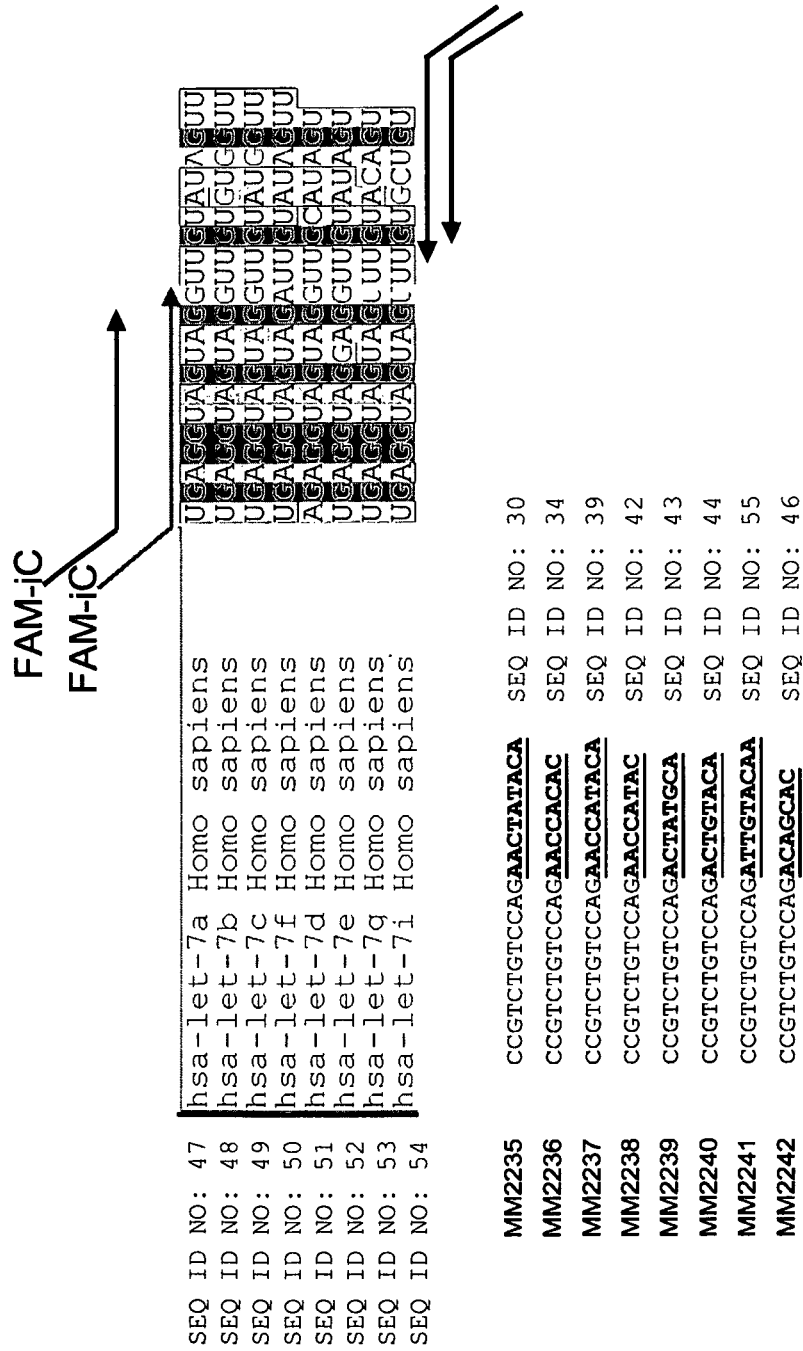
FIG. 1. is an alignment of *Homo sapiens* miRNA let-7 (hsa-let-7) target sequences and amplification primer sequences.

Disclosed herein are methods and materials for detecting and quantifying target nucleic acids. Specifically, the methods disclosed herein can be used to detect and quantify small RNA in a sample. Amplification and quantification of mature small RNA by PCR presents a challenge because the mature small RNA is roughly the size of a standard PCR primer. The approaches described herein provide the advantage of a homogenous assay for small RNA that does not require the use of a probe. The methods may be performed in a multiplex format that permits the determination of expression levels for two or more small RNAs in a single reaction.

In practicing the present invention, many conventional techniques in molecular biology are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonuchotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

Unless defined otherwise, all technical and scientific terms used herein generally have the same meaning as commonly understood by one of ordinary skill in the art to which this invention belongs. As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids. Generally, the nomenclature used herein and the laboratory procedures in cell culture, molecular genetics, organic chemistry, analytical chemistry and nucleic acid chemistry and hybridization described below are those well known and commonly employed in the art. The definitions of certain terms as used in this specification are provided below.

As used herein, when referring to a numerical value, the term "about" means plus or minus 10% of the stated value unless otherwise indicated.

The terms "3'-DNA portion," or "3'-DNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide.

The terms "5'-DNA portion," or "5'-DNA region," "5'-RNA portion," refer to the portion or region of a polynucleotide or oligonucleotide located towards the 5' end of the polynucleotide or oligonucleotide, and may or may not include the 5' most nucleotide or moieties attached to the 5' most nucleotide of the same polynucleotide or oligonucleotide.

As used herein, "amplification" or "amplifying" refers to the production of additional copies of a nucleic acid sequence. Amplification is generally carried out using reverse transcription (RT) and/or polymerase chain reaction (PCR) technologies known in the art. The term "amplification reaction mixture" refers to an aqueous solution comprising the various reagents used to amplify a target nucleic acid. These may include enzymes (e.g., a thermostable polymerase), aqueous buffers, salts, amplification primers, target nucleic acid, and nucleotide triphosphates, and optionally at least one labeled probe and/or optionally at least one agent for determining the melting temperature of an amplified target nucleic acid (e.g., a fluorescent intercalating agent that exhibits a change in fluorescence in the presence of double-stranded nucleic acid).

The terms "assessing" and "evaluating" are used interchangeably to refer to any form of measurement, and include determining if a characteristic, trait, or feature is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. For non-natural bases, as described herein, the base-pairing rules include the formation of hydrogen bonds in a manner similar to the Watson-Crick base pairing rules or by hydrophobic, entropic, or van der Waals forces. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

As used herein, "small RNA" means an RNA molecule containing less than about 50 bases in length and more than about 5 bases in length. "Small RNA" includes but is not limited to biologically active RNA molecules such as microRNA (miRNA), short interfering RNAs (siRNAs), short hairpin RNAs (shRNAs), piRNA (Piwi-interacting RNA) or RNA species derived from aforementioned classes of RNAs by metabolic processes.

As used herein, "microRNA" or "miRNA" refers to an oligoribonucleotide, which suppresses expression of a polynucleotide comprising the target sequence transcript or down regulates a target RNA.

As used herein, a "small RNA precursor" refers to a larger polynucleotide which is processed to produce a mature small RNA, and includes a DNA which encodes an RNA precursor, and an RNA transcript comprising the small RNA. A "mature small RNA" refers to the small RNA generated from the processing of a small RNA precursor. A "small RNA template" is an oligonucleotide region, or regions, in a nucleic acid construct which encodes the small RNA. Typically, a mature small RNA comprises from about 20 to 25 bases.

As used herein, the term "isoform" refers to a members of a small RNA family that differ in their mature sequence. Small RNA isoforms are mature small RNAs that are of nearly identical sequences, usually differing by about 1, 2, 3, 4, or 5 nucleotides. For example, these families are designated with a letter (e.g. let-7b and let-7c). The second type of isoforms are small RNA genes that produce the identical mature small RNA from a different precursor gene (e.g. let-7a-1 and let-7a-2). These are designated with a number implying that both genes, let-7a-1 and let-7a-2, produce the identical mature small RNA (let-7a). Each isoform is usually located in different regions of the genome.

As used herein, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. RNA may be used in the methods described herein and/or may be converted to cDNA by reverse-transcription for use in the methods described herein.

As used herein, the term "sample" is used in its broadest sense. A sample may include a bodily tissue or a bodily fluid including but not limited to blood (or a fraction of blood such as plasma or serum), lymph, mucus, tears, urine, and saliva. A sample may include an extract from a cell, a chromosome, organelle, or a virus. A sample may be a "cell-free" sample, meaning that the volume of cells in the sample are less than about 2% of the total sample volume (preferably less than about 1% of the total sample volume). In some embodiments, a sample may comprise RNA (e.g., miRNA) or cDNA, any of which may be amplified to provide amplified nucleic acid. For example, a sample may include nucleic acid in solution or bound to a substrate (e.g., as part of a microarray). A sample may be obtained from any patient.

The term, "threshold cycle" or "$C_T$" is used in reference to quantitative or real-time analysis methods and indicates the fractional cycle number at which the amount of amplification products, reaches a fixed threshold or limit. Thresholds can be set manually by the user or determined by the software of a real-time instrument.

Sample Preparation

In some embodiments, the methods are used to detect small RNA in a biological sample. The biological sample may be from any organism that has endogenous small RNA. Organisms include, but are not limited to, arthopods (*Drosophila melanogaster*); nematodes (*Caenorhabditis elegans* and *Caenorhabditis briggsae*); vertebrates (*Homo sapiens, Mus musculus, Rattus norvegicus*); plants (*Arabidopsis thaliana* and *Oryza sativa*), all of which have small RNA that has been sequenced. Alternatively, small RNA may be recombinant, such that it is obtained from a cell-free system or reaction mixture or from a recombinant host cell, which may or may not have endogenous small RNA. Furthermore, small RNA may be evaluated in samples that were previously fixed. In some embodiments, the sample may be fixed in formaldehyde or paraformaldehyde prior to taking steps to evaluate its small RNA. In additional embodiments, samples that can be used according to the invention include those in which RNA in the sample has been degraded. Such samples include those in which about or at least about 50%, 60%, 70%, 80%, 90%, 95% or more, or any range derivable therein, of the mRNA and/or rRNA in the sample is degraded. In particular embodiments, samples in which there has been substantial degradation—that is, at least about 80% degradation of mRNA and/or rRNA in the sample—are analyzed according to methods and compositions of the invention.

Small RNA used in the reaction may be obtained by a variety of methods and from a variety of sources. The small RNA may be obtained from a biological sample, such as a cell, tissue, or organ. It may be isolated from a biological sample that contains other RNA molecules as well, such as mRNA, tRNA, and/or rRNA. In certain instances, total RNA is first isolated from the sample and then the small RNA is separated from the other RNA, thereby enriching for small RNA. In some embodiments, the small RNA has been isolated away from other RNA to enrich for the small RNA, such that the small RNA is substantially pure, meaning it is at least about 80%, 85%, 90%, 95% pure or more, but less than 100% pure, with respect to other RNA molecules. Various kits for the extraction of RNA from biological samples are available commercially.

A cell from which a nucleic acid is obtained for use in the methods can be a normal cell or a cell displaying one or more symptom of a particular disease or condition. Thus, a biological sample used in a method of the present invention can be obtained from a cancer cell, neoplastic cell, necrotic cell or cell experiencing a disease or condition set forth below. Those skilled in the art will know or be able to readily determine methods for isolating samples from a cell, fluid or tissue using methods known in the art such as those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998).

Exemplary methods that can be used to isolate a particular cell from other cells in a population include, but are not limited to, Fluorescent Activated Cell Sorting (FACS) as described, for example, in Shapiro, *Practical Flow Cytometry*, 3rd edition Wiley-Liss; (1995), density gradient centrifugation, or manual separation using micromanipulation methods with microscope assistance. Exemplary cell separation devices that are useful in the invention include, without limitation, a Beckman JE-6 centrifugal elutriation system, Beckman Coulter EPICS ALTRA computer-controlled Flow Cytometer-cell sorter, Modular Flow Cytometer from Cytomation, Inc., Coulter counter and channelyzer system, density gradient apparatus, cytocentrifuge, Beckman J-6 centrifuge, EPICS V dual laser cell sorter, or EPICS PROFILE flow cytometer. A tissue or population of cells can also be removed by surgical techniques. For example, a tumor or cells from a tumor can be removed from a tissue by surgical methods, or conversely non-cancerous cells can be removed from the vicinity of a tumor.

A biological sample can be prepared for use in the methods of the present invention by lysing a cell that contains one or more desired nucleic acids. Typically, a cell is lysed under conditions that substantially preserve the integrity of the desired nucleic acid. For example, cells can be lysed or subfractions obtained under conditions that stabilize RNA integrity. Such conditions include, for example, cell lysis in strong denaturants, including chaotropic salts such as guanidine thiocyanate, ionic detergents such as sodium dodecyl sulfate, organic solvents such as phenol, high lithium chloride concentrations or other conditions known in the art to be effective in limiting the activity of endogenous RNases during RNA purification. Additionally, relatively undamaged nucleic acids such as RNA can be obtained from a cell lysed by an enzyme that degrades the cell wall. Cells lacking a cell wall either naturally or due to enzymatic removal can also be lysed by exposure to osmotic stress. Other conditions that can be used to lyse a cell include exposure to detergents, mechanical disruption, sonication, heat, pressure differential such as in a French press device, or Dounce homogenization.

Target Nucleic Acids

As used herein, "target nucleic acid" refers to a nucleic acid suspected to be in a sample and to be detected or quantified in a method or system as disclosed herein. Target nucleic acids contain the target nucleic acid sequences that are actually assayed during an assay procedure. The target can be directly or indirectly assayed. In at least some embodiments, the target nucleic acid, if present in the sample, is used as a template for amplification according to the methods disclosed herein. Target nucleic acid may include a small RNA molecule, including without limitation, a miRNA, a siRNA, a shRNA, or other ncRNA. Typically, the target RNA is 17-29 nucleotides long.

In some embodiments, the target nucleic acid is a small RNA (e.g., a miRNA). More than 900 different miRNAs have been identified in humans according to the miRBase and the microRNA Registry (Griffiths-Jones S. *NAR*, 2004, 32, Database Issue, D109-D111 and Ambros et al. *Curr Biol*, 2003, 13, 807-818). miRNAs have also been identified in the Epstein Barr virus, and are differentially expressed in developmental stages, cell types, and tissues. In particular, differential expression has been observed in mammalian organs and embryonic stem cells.

Diagnostic Assays

In some embodiments, the target nucleic acids are small RNAs, wherein the presence or amount of the small RNA species in a biological sample is correlated with the presence of a disease or medical condition. Accordingly, in some aspects, the present methods can be used to detect small RNA in order to diagnose a disease or medical condition.

In some embodiments, the methods described herein for determining the amount of a target small RNA sequence in a biological sample are used to diagnose and/or assess a disease, condition, or potential condition in a patient. In some embodiments, the amount of a target miRNA in the sample is indicative of the presence or absence of a disease, the disease progression, prognosis, or risk thereof.

In certain embodiments, the methods can be applied to quantify the relative expression (i.e. up-regulation or down-regulation) of certain target small RNA sequences in biological samples. Embodiments of the invention include methods for diagnosing and/or assessing a condition or potential condition in a patient comprising determining the amount of a target miRNA sequence and the amount of a reference sequence in a sample from a patient, for example. The difference in the miRNA in the sample from a patient and the miRNA in a reference sample (e.g. a normal or non-pathologic sample), is indicative of a pathology, prognosis, disease, or condition, or risk thereof, for example. The invention may also be applied in methods to quantify small RNA that are indicative of infectious disease, such as a viral, fungal, or bacterial infection.

A "disease" is a pathological condition; for example, one that can be identified by symptoms or other identifying factors as diverging from a healthy or a normal state. The term "disease" includes disorders, syndromes, conditions, and injuries. Diseases include, but are not limited to, proliferative, inflammatory, immune, metabolic, infectious, and ischemic diseases. Diseases also include neural, immune system, muscular, reproductive, gastrointestinal, pulmonary, cardiovascular, renal, proliferative, and/or cancerous diseases.

It is contemplated that the methods described herein can be used in assays that evaluate differences between stages or progression of disease, such as between hyperplasia, neoplasia, pre-cancer, and cancer, or between a primary tumor and a metastasized tumor. Similarly, the methods described herein are applicable to detect differential expression associated with various tissues, e.g. breast, blood, lymph, colon, liver, pancreatic, prostrate, and lung.

The methods may be used to measure differential expression of small RNAs that are known to be associated with certain diseases. In the case of breast cancer, a target miRNA may be selected from human miRNAs including but not limited to miR-10b, miR-21, miR-29b, miR-17-5p, miR-125b, miR-145, miR-146, and miR-155. For detection of malignant lymphoma, a target miRNA may be selected from human miRNAs including but not limited to miR-155, miR-17, miR-18a, miR-19a, miR-20a, miR-19b, and miR-92. In colorectal cancer, a target miRNA may be selected from human miRNAs including but not limited to the let-7 family, miR-10a, miR-20a, miR-24, miR-29b, miR-31, miR-96, miR-133b, miR-135b, miR-143, miR-145, miR-183, miR-17, miR-18a, miR-19a, miR-19b and miR-92. For hepatocellular carcinoma, the target miRNA may be selected from human miRNAs including but not limited to miR-18, miR-125a, miR-195, miR-199a, miR-200a, and miR-224. In cases of pancreatic cancer, the target miRNA may be selected from human miRNAs including but not limited to miR-21, miR-24, miR-100, miR-103, miR-107, miR-125b, and miR-155. For prostate cancer, the target miRNA may be selected from human miRNAs including but not limited to let-7d, miR-128a, miR-195, and miR-203. In cases of lung cancer, the target miRNA may be selected from human miRNAs including but not limited to the let-7 family, miR-17, miR-18a, miR-19a, miR-20a, miR-19b, miR-92, miR-21, miR-126*, miR-155, miR -200b, miR-205, and miR-210. See, e.g., Wiemer, *Eur. J Cancer* 43:1529-1544 (2007). These target and disease lists are solely exemplary, and not limiting on the claimed methods of detection.

In another aspect, this disclosure provides for the comparison of quantity of small RNA in a subject sample to a reference level. These small RNA may be biomarkers, that is, biochemical features or facets that pertain to a subject and can be used to measure the progression or regression of a disease and/or the effect of a treatment. When compared to a reference level, the expression level of biomarkers described herein can be correlative to a subject's disease state. Thus, biomarkers can be indicative of a diseased or healthy state of a subject. Thus, in one embodiment, similar expression of small RNA in a sample from a subject relative to the reference level indicates the absence of a disease or medical condition in the subject. In another embodiment, a difference in the expression of small RNA in a sample from a subject relative to the reference level indicates the presence or severity of the disease or medical condition in the subject. In yet another embodiment, small RNA expression can be compared to a reference level at different times to monitor disease progression or regression.

As used herein, the term "reference level" refers to an amount or concentration of a biomarker which may be of interest for comparative purposes. In one embodiment, a reference level may be the level of at least one biomarker expressed as an average of the level of the at least one biomarker from samples taken from a control population of healthy subjects. In another embodiment, the reference level may be the level of at least one biomarker in the same subject at an earlier time, i.e., before the present assay. In even another embodiment, the reference level may be the level of at least one biomarker in the subject prior to receiving a treatment regime.

Statistical methods can be used to set thresholds for determining when the expression level in a subject can be considered to be different than or similar to the reference level. As used herein, the phrase "difference of the level" refers to differences in the quantity of a small RNA present in a sample taken from patients having or suspected of having a disease or medical condition as compared to a control. In one embodiment, a small RNA may be present at an elevated amount or at a decreased amount in samples of patients having or suspected of having a disease or medical condition compared to a reference level. In one embodiment, a "difference of a level" may be a statistically significant difference. For example, a difference may be statistically significant if the measured level of the biomarker falls outside of about 1.0 standard deviations, about 1.5 standard deviations, about 2.0 standard deviations, or about 2.5 stand deviations of the mean of any control or reference group.

In addition, statistics can be used to determine the validity of the difference or similarity observed between a patient's gene expression level and the reference level. Useful statistical analysis methods are described in L. D. Fisher & G. vanBelle, *Biostatistics: A Methodology for the Health Sciences* (Wiley-Interscience, NY, 1993). For instance, confidence ("p") values can be calculated using an unpaired 2-tailed t test, with a difference between groups deemed significant if the p value is less than or equal to 0.05.

Oligonucleotides and Specific Primers

An oligonucleotide is a nucleic acid that includes at least two nucleotides. Oligonucleotides used in the methods disclosed herein typically include at least about ten (10) nucleotides and more typically at least about fifteen (15) nucleotides. Oligonucleotides as described herein typically are capable of forming hydrogen bonds with oligonucleotides having a complementary base sequence. These bases may include the natural bases such as A, G, C, T and U, as well as non-natural bases such as iso-C and iso-G. As described herein, a first sequence of an oligonucleotide is described as being 100% complementary with a second sequence of an oligonucleotide when the consecutive bases of the first sequence (read 5' to 3') follow the Watson-Crick rule of base pairing as compared to the consecutive bases of the second sequence (read 3' to 5'). An oligonucleotide may include nucleotide substitutions. For example, an artificial base may be used in place of a natural base such that the artificial base exhibits a specific interaction that is similar to the natural base.

An oligonucleotide may be designed to function as a primer. As used herein, a "primer" for amplification is an oligonucleotide that is complementary to a target nucleotide sequence and leads to addition of nucleotides to the 3' end of the primer in the presence of a DNA or RNA polymerase. The approximately 3-5 nucleotides at the 3' terminus of a primer should generally be identical to the target sequence at a corresponding nucleotide position for optimal expression and/or amplification. The term "primer" includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of a nucleic acid. A "reverse primer" is complementary to the sense-strand of a nucleic acid. Primers which are suitable for amplifying a target nucleic acid are generally capable of specifically hybridizing to the target nucleic acid. In one embodiment, the primers for the methods disclosed herein may be about 10-35 nucleotides in length.

A primer that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm (e.g., BLAST).

A primer that is specific for a target nucleic acid will "hybridize" to the target nucleic acid under suitable conditions. As used herein, "hybridization" or "hybridizing" refers to the process by which a oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. "Hybridizing" sequences which bind under conditions of low stringency are those which bind under non-stringent conditions (6×SSC/50% formamide at room temperature) and remain bound when washed under conditions of low stringency (2×SSC, 42° C.). Hybridizing under high stringency refers to the above conditions in which washing is performed at 2×SSC, 65° C. (where SSC is 0.15M NaCl, 0.015M sodium citrate, pH 7.2).

In some embodiments, the primer oligonucleotides comprise two regions—a target binding region and a tail region. The target binding region exhibits a high degree of complementarity to the target nucleic acid, such that it hybridizes to the target nucleic acid at high stringency. The target binding region is designed to provide a free 3' hydroxyl for polymerase-mediated extension of the primer. Typically the target binding region comprises about 5, 6, 7, 8, 9, 10, 11, or 12 nucleotides which are complementary to the target nucleic acid. The complementarity between the target binding region and the target nucleic acid need not be perfect, i.e., one or more mismatches may be present. For example, 1, 2, 3, or 4 mismatches over a stretch of 12 nucleotides may be allowed, yet still provide a suitable amplification primer—particularly, if the primer is fully complementary to the target nucleic acid at the 3' end of the primer or within 2, 3, or 4 bases of the 3' end of the primer.

In some embodiments of the methods disclosed herein, a sample is suspected to contain multiple isoforms of a small RNA. As described above, mature small RNA isoforms of the same family may differ from one another by 1, 2, 3, 4, or 5 nucleotides. The detection methods described herein are capable of discriminating between related small RNA isoforms. A first specific primer for a first small RNA isoform and a second specific primer for a second small RNA isoform are added to the sample, along with a universal primer. One or more of the primers may further comprise a non-natural nucleotide base having a label. The sequence of each specific primer may differ from another at one terminus or near a terminus (e.g., within 1 base, 2 bases, 3 bases, or 4 bases from the 3' terminus). The sequence of each specific primer may differ from another (e.g., by a single nucleotide, by two nucleotides, or by three nucleotides). Each specific primer may include an identical non-natural nucleotide base and a label (e.g., a fluorescent label). Each of the at least two labels may be different from the other. For example, one label may be fluorescein (FAM) and the other label may be hexachlorofluorescein (HEX).

In some embodiments, the specific primers comprise a 5' tail sequence in the 5' region of the primer. The tail region comprises at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides in length, or any range derivable therein. The sequence of the tail region is typically not complementary to any nucleic acid in the sample. The tails may be designed to improve the specificity of the primers by reducing mispriming during PCR, i.e., the tail sequences can be designed to add about 10° C. to the $T_m$ of the specific primers. For example, the annealing temperature used in the first 1 to 5 cycles of PCR with tailed primers may be about 5° C. to 15° C. lower than the annealing temperature in subsequent PCR cycles. The tail sequence may comprise one or more non-standard bases. In a suitable embodiment, the 5' tail sequences of the first primer and the second primer are different so as to maintain an annealing temperature differential between the two primers. The annealing temperature differential between the 5' tails of the first primer and the second primer may be from about 1° C. to 10° C., from about 1° C. to about 7° C., or from about 1° C. to about 5° C.

As will be apparent from the discussion herein, the relative sizes of the specific primers, as well as the amplified portion of the target nucleic acids, will vary depending upon the particular application. Further, the relative location of the primers along the target nucleic acid will vary. Additionally, the location of the non-natural base and labels used in the methods disclosed herein will vary depending upon application.

Additionally, the length of the primer can affect the temperature at which the primer will hybridize to the target nucleic acid. Generally, a longer primer will form a sufficiently stable hybrid to the target nucleic acid sequence at a higher temperature than will a shorter primer. Further, the presence of high proportion of G or C or of particular non-natural bases in the primer can enhance the stability of a hybrid formed between the primer and the target nucleic acid. This increased stability can be due to, for example, the presence of three hydrogen bonds in a G-C interaction or other non-natural base pair interaction compared to two hydrogen bonds in an A-T interaction.

Stability of a nucleic acid duplex can be estimated or represented by the melting temperature, or "$T_m$." The $T_m$ of a particular nucleic acid duplex under specified conditions is the temperature at which 50% of the population of the nucleic acid duplexes dissociate into single-stranded nucleic acid molecules. The $T_m$ of a particular nucleic acid duplex can be predicted by any suitable method. Suitable methods for determining the $T_m$ of a particular nucleic acid duplex include the Oligo™ software program. Primers suitable for use in the methods and kits disclosed herein can be predetermined based on the predicted $T_m$ of an oligonucleotide duplex that comprises the primer.

When the first primer and second primer are annealed to the target nucleic acid, a gap exists between the 3' terminal nucleotide of the first primer and the 3' terminal nucleotide of the second primer. The gap comprises a number of nucleotides of the target nucleic acid. The gap can be any number of nucleotides provided that the polymerase can effectively incorporate nucleotides into an elongating strand to fill the gap during a round of the PCR reaction (e.g., a round of annealing, extension, denaturation). Typically, a polymerase can place about 30 to about 100 bases per second. Thus, the maximum length of the gap between primers depends upon the amount of time within a round of PCR where the temperature is in a range in which the polymerase is active and the primers are annealed.

The oligonucleotides may include at least one non-natural nucleotide. For example, the oligonucleotides may include at least one nucleotide that includes a nucleobase other than A, C, G, T, or U (e.g., iso-C or iso-G). Where the oligonucleotide is used as a primer for PCR, the amplification mixture may include at least one nucleotide that is labeled with a quencher (e.g., Dabcyl). The labeled nucleotide may include at least one non-natural nucleotide. For example, the labeled nucleotide may include at least one nucleobase that is not A, C, G, T, or U (e.g., iso-C or iso-G).

In some embodiments, the oligonucleotide may be designed to avoid forming an intramolecular structure such as a hairpin. In other embodiments, the oligonucleotide may be designed to form an intramolecular structure such as a hairpin. For example, the oligonucleotide may be designed to form a hairpin structure that is altered after the oligonucleotide hybridizes to a target nucleic acid, and optionally, after the target nucleic acid is amplified using the oligonucleotide as a primer (See, e.g., U.S. Pat. No. 5,928,869).

The oligonucleotide may be labeled with a fluorophore that exhibits quenching when incorporated in an amplified product as a primer. In other embodiments, the oligonucleotide may emit a detectable signal after the oligonucleotide is incorporated in an amplified product as a primer. Such primers are known in the art (e.g., LightCycler primers, Ampliflour® Primers, Scorpion® Primers and Lux™ Primers). The fluorophore used to label the oligonucleotide may emit a signal when intercalated in double-stranded nucleic acid. As such, the fluorophore may emit a signal after the oligonucleotide is used as a primer for amplifying the nucleic acid.

The disclosed methods may be performed with any suitable number of oligonucleotides. Where a plurality of oligonucleotides are used (e.g., two or more oligonucleotides), different oligonucleotides may be labeled with different fluorescent dyes capable of producing a detectable signal. In some embodiments, oligonucleotides are labeled with at least one of two different fluorescent dyes. In further embodiments, oligonucleotides are labeled with at least one of three different fluorescent dyes. In some embodiments, each different fluorescent dye emits a signal that can be distinguished from a signal emitted by any other of the different fluorescent dyes that are used to label the oligonucleotides. For example, the different fluorescent dyes may have wavelength emission maximums all of which differ from each other by at least about 5 nm (preferably by least about 10 nm). In some embodiments, each different fluorescent dye is excited by different wavelength energies. For example, the different fluorescent dyes may have wavelength absorption maximums all of which differ from each other by at least about 5 nm (preferably by at least about 10 nm).

As used herein, "universal primer" refers to a primer that can specifically hybridize to two or more different target nucleic acids in a sample (e.g., 3 or more, 4 or more, 5 or more, 10 or more, 15 or more, or 25 or more different target nucleic acids in a sample). A "universal primer" may hybridize to a region of the different target nucleic acids that is identical or that has substantial identity to provide for specific hybridization of the "universal primer" to the different target nucleic acids. A "universal primer" may be complementary to a nucleic acid sequence that is common to all the target nucleic acids being detected in a sample.

Amplification

Disclosed herein are methods for detecting a target small RNA that may utilize RT-PCR and/or PCR. The methods may involve a polymerase, a first primer, a second primer, and optionally, additional primers. Traditional PCR methods include the following steps: denaturation, or melting of double-stranded nucleic acids; annealing of primers; and extension of the primers using a polymerase. This cycle is repeated by denaturing the extended primers and starting again. The number of copies of the target sequence in principle grows exponentially. In practice, it typically doubles with each cycle until reaching a plateau at which more primer-template accumulates than the enzyme can extend during the cycle; then the increase in target nucleic acid becomes linear. An RT-PCR method includes an initial reverse transcription step to produce cDNA from RNA.

In some embodiments, a first primer (i.e., a cDNA primer) is allowed to anneal to the target small RNA. A primer extension reaction using a nucleic acid polymerase (i.e., a reverse transcriptase) extends the annealed specific primer to form a partially-double stranded product. Typically, the first step of extending is performed at a temperature from about 15° C. to about 50° C. The actual temperature of extension may be calculated by one of skill in the art based on the $T_m$ of the target binding region of the cDNA primer.

After primer extension, the cDNA is amplified using PCR. The partially-double stranded product is denatured by heating and then the second primer is allowed to anneal to the cDNA. Typically the first annealing step is performed at a temperature from about 35° C. to about 45° C. or from about 35° C. to about 55° C. The actual temperature of annealing may be calculated by one of skill in the art based on the $T_m$ of the target binding region of the second primer. Subsequent annealing steps may be performed at a higher temperature, e.g., at least about 55° C., because the tail regions of the first and second primers increase the $T_m$ of the primers relative to the amplicon.

One of the two strands of the product may incorporate a non-natural nucleotide base and the fluorescent label from the specific primer. As PCR progresses, the labeled strand is annealed with the primer, which in turn is extended in the opposite direction until the polymerase reaches the non-natural nucleotide base (e.g., isocytosine) and terminates extension with the addition of the complementary non-natural base (e.g., isoguanosine) bearing a fluorescent quencher such as dabcyl. PCR is run for the desired number of cycles to obtain this double-stranded amplification product. As more of the double stranded amplification product accumulates having both a fluorophore and a fluorescent quencher, the fluorescent signal from the specific primer(s) being incorporated into the amplified product will decrease.

The amplification methods described herein may include "real-time monitoring" or "continuous monitoring." These terms refer to monitoring multiple times during a cycle of PCR, such as during temperature transitions and/or temperature hold steps. The term "homogeneous detection assay" is used to describe an assay that includes coupled amplification and detection, which may include "real-time monitoring" or "continuous monitoring." By contrast, "end-point monitoring" refers to the detection of amplification at the termination of a reaction. For example, end-point monitoring may include melting curve analysis and gel electrophoresis and visualization with dyes or autoradiography.

Polymerases

Disclosed herein are methods that may utilize an amplification reaction, e.g., the polymerase chain reaction, to detect nucleic acids of interest in a sample (i.e., nucleic acids of the target and non-target species or subspecies). Suitable nucleic acid polymerases include, for example, polymerases capable of extending an oligonucleotide by incorporating nucleic acids complementary to a template oligonucleotide. For example, the polymerase can be a DNA polymerase.

Enzymes having polymerase activity catalyze the formation of a bond between the 3' hydroxyl group at the growing end of a nucleic acid primer and the 5' phosphate group of a nucleotide triphosphate. These nucleotide triphosphates are usually selected from deoxyadenosine triphosphate (A), deoxythymidine triphosphate (T), deoxycytosine triphosphate (C) and deoxyguanosine triphosphate (G). However, in at least some embodiments, polymerases useful for the methods disclosed herein also may incorporate non-natural bases using nucleotide triphosphates of those non-natural bases.

Because the relatively high temperatures necessary for strand denaturation during methods such as PCR can result in the irreversible inactivation of many nucleic acid polymerases, nucleic acid polymerase enzymes useful for performing the methods disclosed herein preferably retain sufficient polymerase activity to complete the reaction when subjected to the temperature extremes of methods such as PCR. In some embodiments, the nucleic acid polymerase enzymes useful for the methods disclosed herein are thermostable nucleic acid polymerases. Suitable thermostable nucleic acid polymerases include, but are not limited to, enzymes derived from thermophilic organisms. Examples of thermophilic organisms from which suitable thermostable nucleic acid polymerase can be derived include, but are not limited to, *Thermus aquaticus, Thermus thermophilus, Thermus flavus, Thermotoga neapolitana* and species of the *Bacillus, Thermococcus, Sulfobus,* and *Pyrococcus* genera. Thermostable polymerases may also be derived from thermostable bacteriophage isolated from thermophilic organisms. Nucleic acid polymerases can be purified directly from these thermophilic organisms and thermostable phages and/or may be recombinantly expressed and isolated from a suitable system such as *Escherichia coli* cells. Suitable thermostable nucleic acid polymerases, such as those described above, are commercially available.

Polymerases can "misincorporate" bases during PCR. In other words, the polymerase can incorporate a nucleotide (for example adenine) at the 3' position on the synthesized strand that does not form canonical hydrogen base pairing with the paired nucleotide (for example, cytosine) on the template nucleic acid strand. The PCR conditions can be altered to decrease the occurrence of misincorporation of bases. For example, reaction conditions such as temperature, salt concentration, pH, detergent concentration, type of metal, concentration of metal, and the like can be altered to decrease the likelihood that polymerase will incorporate a base that is not complementary to the template strand.

As an alternative to using a single polymerase, any of the methods described herein can be performed using multiple enzymes. For example, it will be recognized when RNA is used as a sample, a reverse transcriptase can be used to transcribe the RNA to cDNA (e.g., AMV or MMLv). The reverse transcription may occur prior to PCR amplification.

Non-Natural Bases

As contemplated in the methods and kits disclosed herein, at least one primer typically comprises at least one non-natural base. DNA and RNA are oligonucleotides that include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytosine (C), and uridine (U). These five bases are "natural bases". According to the rules of base pairing elaborated by Watson and Crick, the natural bases can hybridize to form purine-pyrimidine base pairs, where G pairs with C and A pairs with T or U. These pairing rules facilitate specific hybridization of an oligonucleotide with a complementary oligonucleotide.

The formation of these base pairs by the natural bases is facilitated by the generation of two or three hydrogen bonds between the two bases of each base pair. Each of the bases includes two or three hydrogen bond donor(s) and hydrogen bond acceptor(s). The hydrogen bonds of the base pair are each formed by the interaction of at least one hydrogen bond donor on one base with a hydrogen bond acceptor on the other base. Hydrogen bond donors include, for example, heteroatoms (e.g., oxygen or nitrogen) that have at least one attached hydrogen. Hydrogen bond acceptors include, for example, heteroatoms (e.g., oxygen or nitrogen) that have a lone pair of electrons.

The natural bases, A, G, C, T, and U, can be derivatized by substitution at non-hydrogen bonding sites to form modified natural bases. For example, a natural base can be derivatized for attachment to a support by coupling a reactive functional group (for example, thiol, hydrazine, alcohol, amine, and the like) to a non-hydrogen bonding atom of the base. Other possible substituents include, for example, biotin, digoxigenin, fluorescent groups, alkyl groups (e.g., methyl or ethyl), and the like.

As used herein, the term "non-natural base" means a base other than A, G, C, T, or U that is susceptible of incorporation into an oligonucleotide which is capable of base-pairing by hydrogen bonding, or by hydrophobic, entropic, or van der Waals interactions to form base pairs with a complementary non-natural base. Non-natural bases, which form hydrogen-bonding base pairs, can also be constructed as described, for example, in U.S. Pat. Nos. 5,432,272; 5,965,364; 6,001,983; 6,037,120, all of which are incorporated herein by reference. Suitable bases and their corresponding base pairs may include the following bases in base pair combinations (iso-C/iso-G, K/X, H/J, and M/N):

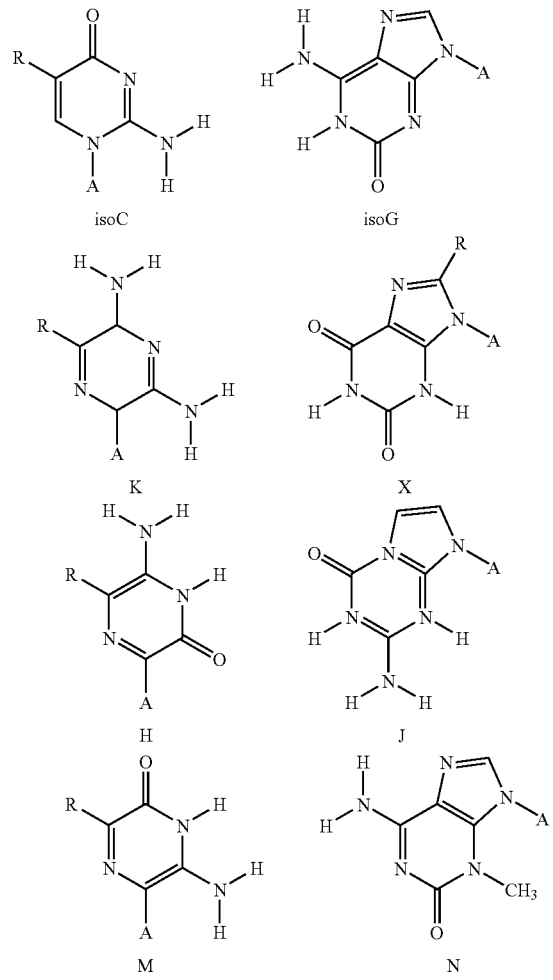

where A is the point of attachment to the sugar or other portion of the polymeric backbone and R is H or a substituted or unsubstituted alkyl group. It will be recognized that other non-natural bases utilizing hydrogen bonding can be prepared, as well as modifications of the above-identified non-natural bases by incorporation of functional groups at the non-hydrogen bonding atoms of the bases.

The hydrogen bonding of these non-natural base pairs is similar to those of the natural bases where two or three hydrogen bonds are formed between hydrogen bond acceptors and hydrogen bond donors of the pairing non-natural bases. One of the differences between the natural bases and these non-natural bases is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-natural bases for use in oligonucleotides include, for example, naphthalene, phenanthrene, and pyrene derivatives as discussed, for example, in Ren et al., *J. Am. Chem. Soc.* 118, 1671 (1996) and McMinn et al., *J. Am. Chem. Soc.* 121, 11585 (1999), both of which are incorporated herein by reference. These bases do not utilize hydrogen bonding for stabilization, but instead rely on hydrophobic or van der Waals interactions to form base pairs.

Labels

In accordance with the methods and kits disclosed herein, the primers and/or the added non-natural nucleotide base (such as a non-natural nucleotide triphosphate) may comprise a label. Nucleotides and oligonucleotides can be labeled by incorporating moieties detectable by spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

As used herein, "labels" are chemical or biochemical moieties useful for labeling a nucleic acid (including a single nucleotide), amino acid, or antibody. "Labels" include fluorescent agents, chemiluminescent agents, chromogenic agents, quenching agents, radionuclides, enzymes, substrates, cofactors, inhibitors, magnetic particles, and other moieties known in the art. "Labels" or "reporter molecules" are capable of generating a measurable signal and may be covalently or noncovalently joined to an oligonucleotide or nucleotide (e.g., a non-natural nucleotide).

A variety of labels which are appropriate for use in the methods and kits, as well as methods for their inclusion in the probe, are disclosed herein and are known in the art. These include, but are not limited to, enzyme substrates, fluorescent dyes, chromophores, chemiluminescent labels, electrochemiluminescent labels, such as ORI-TAG™ (Igen), ligands having specific binding partners, or any other labels that can interact with each other to enhance, alter, or diminish a signal. It is understood that, should the PCR be practiced using a thermocycler instrument, a label should be selected to survive the temperature cycling required in this automated process.

In some embodiments, the primers used in the methods are labeled. For example, the oligonucleotides may include a label that emits a detectable signal. By way of example, the label system may be used to produce a detectable signal based on a change in fluorescence, fluorescence resonance energy transfer (FRET), fluorescence quenching, phosphorescence, bioluminescence resonance energy transfer (BRET), or chemiluminescence resonance energy transfer (CRET).

In some embodiments, two interactive labels may be used on a single oligonucleotide with due consideration given for maintaining an appropriate spacing of the labels. In other embodiments, two interactive labels on different oligonucleotides may be used, such as, for example, the reporter and the second region of the second primer. In this embodiment, the reporter and the second region are designed to hybridize to each other. Again, consideration is given to maintaining an appropriate spacing of the labels between the oligonucleotides when hybridized.

The oligonucleotides and nucleotides (e.g., non-natural nucleotides) of the disclosed methods may be labeled with a "fluorescent dye" or a "fluorophore." As used herein, a "fluorescent dye" or a "fluorophore" is a chemical group that can be excited by light to emit fluorescence. Some suitable fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes and/or dyes sold under the following tradenames: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC 18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer −1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP(S65T); GFP red shifted (rs-GFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 4G; Sevron Brilliant Red 2B; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF 1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC Tetramethyl-RodamineIsoThioCyanate; True Blue; TruRed; Ultralite; Uranine B; Uvitex SFC; VIC®; wt GFP; WW 781;

X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The oligonucleotides and nucleotides of the disclosed methods (e.g., non-natural nucleotide triphosphates) may be labeled with a quencher. Quenching may include dynamic quenching (e.g., by FRET), static quenching, or both. Suitable quenchers may include Dabcyl. Suitable quenchers may also include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

The oligonucleotides or nucleotides (e.g., non-natural nucleotides) of the present methods may be labeled with a donor fluorophore and an acceptor fluorophore (or quencher dye) that are present in the oligonucleotides at positions that are suitable to permit FRET (or quenching). Labeled oligonucleotides that are suitable for the present methods may include but are not limited to oligonucleotides designed to function as LightCycler primers or probes, Taqman® Probes, Molecular Beacon Probes, Amplifluor® Primers, Scorpion® Primers, and Lux™ Primers.

The labels can be attached to the nucleotides, including non-natural bases, or oligonucleotides directly or indirectly by a variety of techniques. Depending upon the precise type of label used, the label can be located at the 5' or 3' end of the oligonucleotide, located internally in the oligonucleotide sequence, or attached to spacer arms extending from the oligonucleotide and having various sizes and compositions to facilitate signal interactions. Using commercially available phosphoramidite reagents, one can produce oligonucleotides containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite, and can label them using protocols described in, for example, *PCR Protocols: A Guide to Methods and Applications*, ed. by Innis et al., Academic Press, Inc., 1990, incorporated herein by reference. The label can be indirectly attached to a nucleotide or oligonucleotide using a suitable spacer or chemical linker.

Methods for incorporating oligonucleotide functionalizing reagents having one or more sulfhydryl, amino or hydroxyl moieties into the oligonucleotide reporter sequence, typically at the 5' terminus, are described in U.S. Pat. No. 4,914,210, incorporated herein by reference. For example, 5' phosphate group can be incorporated as a radioisotope by using polynucleotide kinase and [$\gamma^{32}$P]ATP to provide a reporter group. Biotin can be added to the 5' end by reacting an aminothymidine residue, introduced during synthesis, with an N-hydroxysuccinimide ester of biotin. Labels at the 3' terminus, for example, can employ polynucleotide terminal transferase to add the desired moiety, such as for example, cordycepin, $^{35}$S-dATP, and biotinylated dUTP.

Oligonucleotide derivatives are also available as labels. For example, etheno-dA and etheno-A are known fluorescent adenine nucleotides which can be incorporated into a an oligonucleotide. Similarly, etheno-dC is another analog that can be used in reporter synthesis. The oligonucleotides containing such nucleotide derivatives can be hydrolyzed to release much more strongly fluorescent mononucleotides by the polymerase's 5' to 3' nuclease activity as nucleic acid polymerase extends a primer during PCR.

In another embodiment, the system for detection comprises a pair of interactive signal-generating labels effectively positioned on the oligonucleotide and on a second component of the assay (such as the labeled nucleotide triphosphate), so as to quench the generation of detectable signal when the interactive signal-generating labels are in sufficiently close proximity to each other. Separation of the interactive signal-generating moieties results in the production of a detectable signal. Examples of such labels include dye/quencher pairs or two dye pairs (where the emission of one dye stimulates emission by the second dye).

In an exemplified embodiment, the interactive signal generating pair comprises a fluorophore and a quencher that can quench the fluorescent emission of the fluorophore, as described herein. For example, a quencher may include dimethylaminoazobenzen aminoexal-3-acryinido (Dabcyl, also known as Methyl Red) and the fluorophore may be FAM or HEX. Other fluorophore-quencher pairs have been described in Morrison, *Detection of Energy Transfer and Fluorescence Quenching in Nonisotopic Probing, Blotting and Sequencing*, Academic Press, 1995.

In one embodiment, these interactive signal-generating labels can be used in a detection method where the second region of the second primer comprises at least one non-natural base and a label. The second label of the pair is provided by at least one non-natural base that is complementary to the non-natural base of the primer, and a second label. For example, if a dye/quencher pair is used, incorporation of the at least one non-natural base into the amplification product will result in a reduction of fluorescence.

Alternatively, the proximity of the two labels can be detected using fluorescence resonance energy transfer (FRET) or fluorescence polarization. FRET is a distance-dependent interaction between the electronic excited states of two dye molecules in which excitation is transferred from a donor molecule to an acceptor molecule without emission of a photon. Examples of donor/acceptor dye pairs for FRET are known in the art and may include fluorophores and quenchers described herein such as Fluorescein/Tetramethylrhodamine, IAEDANS™/Fluorescein (Molecular Probes, Eugene, Oreg.), EDANS™/Dabcyl, Fluorescein/Fluorescein (Molecular Probes, Eugene, Oreg.), BODIPY™ FL/BODIPY™ FL (Molecular Probes, Eugene, Oreg.), and Fluorescein/QSY7™.

Incorporation of a Reporter Comprising Non-Natural Bases

In some embodiments, a region of the primers comprises a non-natural base. A non-natural nucleotide triphosphate that is complementary to the non-natural base present in the first and/or second primer is incorporated into the amplification product using a suitable enzyme. In suitable embodiments the second non-natural nucleotide triphosphate is conjugated to a label, which interacts with the label in the first and/or second primer. In this embodiment, the incorporation of the non-natural base is correlated with the presence of the target nucleic acid in the sample.

The disclosed methods and kits may employ a nucleic acid polymerase and one or more primers specific for one or more target nucleic acids. The PCR reaction mixture may include the four naturally occurring deoxynucleotide triphosphates (i.e., dATP, dCTP, dGTP, and dTTP) as well as one or more non-natural nucleotide triphosphate (i.e., d-iCTP, d-iGTP) as the reporter. In some embodiments, the one or more non-natural nucleotide triphosphates in the reaction mixture comprises a label, which may include a dye and/or a quencher.

The polymerase is used to synthesize a single strand from the 3'-OH end of each primer using polymerase chain reaction. The polymerase chain reaction is allowed to proceed for the desired number of cycles, to obtain an amplification product. In some embodiments, the non-natural base of the reporter comprises a nucleotide triphosphate base that is complementary to the non-natural base of the single-stranded region of the amplification product. In this embodiment, the PCR reaction includes the presence of labeled non-natural nucleotide triphosphate base, in addition to the four naturally occurring nucleotide triphosphate bases (i.e., dATP, dCTP, dGTP, and dTTP). The concentration of non-natural nucleotide triphosphate base in the PCR reaction can range, for example, from 1 μM to 100 μM. The non-natural nucleotide triphosphate base may include a label.

Suitable enzymes for incorporation of the reporter into the amplification product include, for example, polymerases and ligases. A number of polymerases that are capable of incorporating natural nucleotides into an extending primer chain can also incorporate a non-natural base into an amplification product opposite a complementary non-natural base. Typically, class A DNA polymerases; such as Klenow, Tfl, Tth, Taq, Hot Tub, and Bst, are better able than class B polymerases; such as Pfu, Tli, Vent exo-, T4, and Pwo, to incorporate a non-natural base. Reverse transcriptases, such as HIV-1, can also be used to incorporate non-natural bases into an extending primer opposite its complementary non-natural base within a template. In this embodiment, the polymerase can be nuclease deficient or can have reduced nuclease activity. While not intended to limit the disclosed methods and kits, nuclease deficient polymerases are expected to be more robust because nuclease activities have been shown to interfere with some PCR reactions (*Gene* 1992 112(1):29-35 and *Science* 1993 260(5109):778-83).

Detection

Detection and analysis of the target nucleic acids can be accomplished using any methods known in the art. Numerous methods are available for the detection of nucleic acids containing any of the above-listed labels. For example, biotin-labeled oligonucleotide(s) can be detected using non-isotopic detection methods which employ avidin conjugates such as streptavidin-alkaline phosphatase conjugates. Fluorophore-labeled oligonucleotide(s) can be detected using a fluorescence-imager.

Presence of the target nucleic acid in the sample is determined by correlating the presence of the labeled non-natural nucleotide and/or labeled oligonucleotide in the amplification product. Suitable detection and visualization methods are used to detect the target nucleic acid. For example, presence of the target nucleic acid may be determined by detecting the label by fluorescence or other visualization method. Fluorescence polarization, for example, can be used to detect the incorporation of the reporter into the amplification product.

In some embodiments, a reporter comprises a non-natural base (which is complementary to a non-natural base present in the primer), and a quencher. In this embodiment, the non-natural base of the primer includes a fluorophore. Incorporation of the reporter brings the quencher into proximity with the fluorophore. This, in turn, reduces the signal output of the fluorophore, and this reduction in signal can be detected and correlated with the presence of the target nucleic acid. Suitable fluorophore-quencher pairs are discussed above. Alternatively, a dye-dye pair can be used for fluorescence induction. When the target nucleic acid is present, PCR creates a duplexed product that places the two dyes in close proximity, and the fluorescent output of the label changes. The change is detectable by bench-top fluorescent plate readers or using a real-time PCR detection system.

In one embodiment, when the target is present, a duplexed product is created that places the first and second labels (e.g. fluorophore/quencher pair) into close proximity. When the two labels are in close proximity, the fluorescent output of the reporter molecule label changes. The change is detectable by most bench-top fluorescent plate readers. Alternatively, the label pair comprises a quencher-label pair in close proximity. In this embodiment, the fluorescent output of the reporter molecule label changes, and this change is detectable. Other suitable detection methods are contemplated for used in the disclosed methods and kits.

In another embodiment, the labels are detected after further processing. It is contemplated that the reporter oligonucleotide fragments can be separated from the reaction using any of the many techniques known in the art useful for separating oligonucleotides. For example, the reporter oligonucleotide fragments can be separated from the reaction mixture by solid phase extraction. The reporter oligonucleotide fragments can be separated by electrophoresis or by methods other than electrophoresis. For example, biotin-labeled oligonucleotides can be separated from nucleic acid present in the reaction mixture using paramagnetic or magnetic beads, or particles which are coated with avidin (or streptavidin). In this manner, the biotinylated oligonucleotide/avidin-magnetic bead complex can be physically separated from the other components in the mixture by exposing the complexes to a magnetic field. In one embodiment, reporter oligonucleotide fragments are analyzed by mass spectrometry.

In some embodiments, when amplification is performed and detected on an instrument capable of reading fluorescence during thermal cycling, the intended PCR product from non-specific PCR products can be differentiated using a melting-curve analysis. Increasing the temperature of the reaction which contains the non-specific reaction products to above the $T_m$ of the duplexed DNAs and intended product may melt the DNA duplex of the non-specific products and disrupt the interaction of the labels giving a measurable change in fluorescence. By measuring the change in fluorescence while gradually increasing the temperature of the reaction subsequent to amplification and signal generation it may be possible to determine the $T_m$ of the intended product as well as that of the nonspecific product. A non-specific product may also be detected during amplification by reading the signal during the extension step (e.g., at 72° C.). If the $T_m$ of the non-specific product is less than the temperature, then the signal from one or more labels will be detected.

Where the oligonucleotides are labeled with a first fluorescent dye, determining the melting temperature of the detected nucleic acid may include observing a signal from a second fluorescent dye that is different from the first fluorescent dye. In some embodiments, the second fluorescent dye for determining the melting temperature of the detected nucleic acid is an intercalating agent. Suitable intercalating agents may include, but are not limited to SYBR™ Green 1 dye, SYBR dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-amino-actinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixture thereof. In suitable embodiments, the selected intercalating agent is SYBR™ Green 1 dye.

Typically, an intercalating agent used in the method will exhibit a change in fluorescence when intercalated in double-stranded nucleic acid. A change in fluorescence may include an increase in fluorescence intensity or a decrease in fluorescence intensity. For example, the intercalating agent may exhibit a increase in fluorescence when intercalated in double-stranded nucleic acid, and a decrease in fluorescence when the double-stranded nucleic acid is melted. A change in fluorescence may include a shift in fluorescence spectra (i.e., a shift to the left or a shift to the right in maximum absorbance wavelength or maximum emission wavelength). For example, the intercalating agent may emit a fluorescent signal of a first wavelength (e.g., green) when intercalated in double-stranded nucleic and emit a fluorescent signal of a second wavelength (e.g., red) when not intercalated in double-stranded nucleic acid. A change in fluorescence of an intercalating agent may be monitored at a gradient of temperatures to determine the melting temperature of the nucleic acid (where the intercalating agent exhibits a change in fluorescence when the nucleic acid melts).

In the disclosed methods, each of these amplified target nucleic acids may have different melting temperatures. For example, each of these amplified target nucleic acids may have a melting temperature that differs by at least about 1° C., more preferably by at least about 2° C., or even more preferably by at least about 4° C. from the melting temperature of any of the other amplified target nucleic acids.

Kits

Reagents employed in the disclosed methods can be packaged into diagnostic kits. Diagnostic kits include at least a first and second primer. In some embodiments the kit includes non-natural bases capable of being incorporated into an elongating oligonucleotide by a polymerase. In one embodiment, the non-natural bases are labeled. If the oligonucleotide and non-natural base are unlabeled, the specific labeling reagents can also be included in the kit. The kit can also contain other suitably packaged reagents and materials needed for amplification, for example, buffers, dNTPs, or polymerizing enzymes, and for detection analysis, for example, enzymes and solid phase extractants. In various aspects, the kits may comprise multiple amplification primer sets, wherein at least one of the primers in each of the primer sets comprises a sequence that is complementary to a portion of at least two small RNAs, such as a target miRNA.

In some embodiments, kits include one or more of the following (consistent with methods, reagents, and compositions discussed above): components for sample purification, including a lysis buffer with a chaotropic agent; a glass-fiber filter or column; an elution buffer; a wash buffer; an alcohol solution; and a nuclease inhibitor. The components of the kits may be packaged either in aqueous media or in lyophilized form, for example, and will be provided in a suitable container. The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Reagents useful for the disclosed methods can be stored in solution or can be lyophilized. When lyophilized, some or all of the reagents can be readily stored in microtiter plate wells for easy use after reconstitution. It is contemplated that any method for lyophilizing reagents known in the art would be suitable for preparing dried down reagents useful for the disclosed methods.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

EXAMPLES

The present methods and kits, thus generally described, will be understood more readily by reference to the following examples, which are provided by way of illustration and are not intended to be limiting of the present methods and kits.

Example 1

Detection of LET7 miRNA

Primer Design. Forward and cDNA primers were designed to amplify and detect *Homo sapiens* micro RNA let7 (hsa-let-7) sequences (Table 1) according to miRBase, (*Nucleic Acids Research*, 2008, Vol. 36, Database issue D154-D158). Primer sequences are given in Table 2.

TABLE 1

*Homo sapiens* miRNA let7 (hsa-let-7) sequences.

| Name | Sequence | SEQ ID NO |
| --- | --- | --- |
| hsa-let-7a | UGAGGUAGUAGGUUGUAUAGUU | 47 |
| hsa-let-7b | UGAGGUAGUAGGUUGUGUGGUU | 48 |
| hsa-let-7c | UGAGGUAGUAGGUUGUAUGGUU | 49 |
| hsa-let-7f | UGAGGUAGUAGAUUGUAUAGUU | 50 |
| hsa-let-7d | AGAGGUAGUAGGUUGCAUAGU | 51 |
| hsa-let-7e | UGAGGUAGGAGGUUGUAUAGU | 52 |
| hsa-let-7g | UGAGGUAGUAGUUUGUACAGU | 53 |
| hsa-let-7i | UGAGGUAGUAGUUUGUGCUGU | 54 |

The primers shown in Table 2 comprise two portions. The 3' portion of the two part cDNA primers is designed to be complementary to the 3' portion of the target miRNA sequences. The second portion of the cDNA primers contains a 5' target-independent tail sequence to increase the $T_m$ to allow PCR cycling following a single initial extension reaction at a lower annealing temperature. The analyte-specific first portion of various cDNA primers are specific sequences to individual miRNAs or to groups of let-7 family members.

The first portion of the forward PCR primers is complementary to the 3' end of the bi-partitite miRNA cDNA extension product. The second portion of the cDNA primers also contains a 5' target-independent tail sequence to increase the $T_m$ to allow PCR cycling following a single initial extension reaction at a lower annealing temperature. The forward primer may be designed to amplify all the let-7 miRNAs or it can be designed to only amplify a subset of the let-7 species by extension from a specific 3' base. A diagram depicting exemplary let-7 primer designs is shown in FIG. 1.

The forward and/or cDNA primers also contained 5' iC and fluorophores, such as 6-carboxy-fluorescein (FAM) and hexachlorofluorescein (HEX). This modification allowed detection of amplification using real-time detection when amplification is performed in the presence of dabcyl-d-iGTP. Primer sequences are given in Table 2. In Table 2 the character "X" is defined to represent d-iC.

TABLE 2

Primer Sequences

| SEQ ID NO | Name | Sequence 5'-3' | Purpose |
|---|---|---|---|
| 1 | MM2261 | UGAGGUAGUAGGUUGUAUAGUU | RNA target |
| 2 | MM2262 | UGAGGUAGUAGGUUGUAUGGUU | RNA target |
| 3 | MM2263 | UGAGGUAGUAGAUUGUAUAGUU | RNA target |
| 4 | MM2282 | UGAGGUAGUAGUUUGUACAGU | RNA target |
| 5 | MM2287 | GTGTCCATGAGGTAGTAG | Forward Primer |
| 6 | MM2243 | FAM-XGTGTCCATGAGGTAGTAG | Forward Primer |
| 7 | MM2291 | HEX-XGTGTCCATGAGGTAGTAG | Forward Primer |
| 8 | MM2304 | FAM-XCGTGTCCATGAGGTAGTAG | Forward Primer |
| 9 | MM2308 | FAM-XGCACAGGTTGAGGTAGTAG | Forward Primer |
| 10 | MM2288 | GTGTCCATGAGGTAGTAGG | Forward Primer |
| 11 | MM2244 | FAM-XGTGTCCATGAGGTAGTAGG | Forward Primer |
| 12 | MM2292 | HEX-XGTGTCCATGAGGTAGTAGG | Forward Primer |
| 13 | MM2305 | FAM-XCGTGTCCATGAGGTAGTAGG | Forward Primer |
| 14 | MM2309 | FAM-XGCACAGGTTGAGGTAGTAGG | Forward Primer |
| 15 | MM2289 | GTGTCCATGAGGTAGTAGA | Forward Primer |
| 16 | MM2245 | FAM-XGTGTCCATGAGGTAGTAGA | Forward Primer |
| 17 | MM2293 | HEX-XGTGTCCATGAGGTAGTAGA | Forward Primer |
| 18 | MM2306 | FAM-XCGTGTCCATGAGGTAGTAGA | Forward Primer |
| 19 | MM2310 | FAM-XGCACAGGTTGAGGTAGTAGA | Forward Primer |
| 20 | MM2290 | GTGTCCATGAGGTAGTAGT | Forward Primer |
| 21 | MM2246 | FAM-XGTGTCCATGAGGTAGTAGT | Forward Primer |
| 22 | MM2307 | FAM-XCGTGTCCATGAGGTAGTAGT | Forward Primer |
| 23 | MM2311 | FAM-XGCACAGGTTGAGGTAGTAGT | Forward Primer |
| 24 | MM2298 | FAM-XGGCAGACAGGACAACTATAC | cDNA Primer |
| 25 | MM2299 | HEX-XGGCAGACAGGACAACTATAC | cDNA Primer |
| 26 | MM2300 | FAM-XGGCAGACAGGACAACTATA | cDNA Primer |
| 27 | MM2301 | HEX-XGGCAGACAGGACAACTATA | cDNA Primer |
| 28 | MM2294 | FAM-XCCGTCTGTCCAGAACTATAC | cDNA Primer |
| 29 | MM2295 | HEX-XCCGTCTGTCCAGAACTATAC | cDNA Primer |
| 30 | MM2235 | CCGTCTGTCCAGAACTATACA | cDNA Primer |
| 31 | MM2284 | CCGTCTGTCCAGAACTATAC | cDNA Primer |

TABLE 2-continued

Primer Sequences

| SEQ ID NO | Name | Sequence 5'-3' | Purpose |
|---|---|---|---|
| 32 | MM2285 | CCGTCTGTCCAGAACTATA | cDNA Primer |
| 33 | MM2286 | CCGTCTGTCCAGAACTAT | cDNA Primer |
| 34 | MM2236 | CCGTCTGTCCAGAACCACAC | cDNA Primer |
| 35 | MM2256 | CCGTCTGTCCAGAACCACACA | cDNA Primer |
| 36 | MM2257 | CCGTCTGTCCAGAACCACACAA | cDNA Primer |
| 37 | MM2302 | FAM-XGGCAGACAGGACAACCATAC | cDNA Primer |
| 38 | MM2303 | HEX-XGGCAGACAGGACAACCATAC | cDNA Primer |
| 39 | MM2237 | CCGTCTGTCCAGAACCATACA | cDNA Primer |
| 40 | MM2296 | FAM-XCCGTCTGTCCAGAACCATAC | cDNA Primer |
| 41 | MM2297 | HEX-XCCGTCTGTCCAGAACCATAC | cDNA Primer |
| 42 | MM2238 | CCGTCTGTCCAGAACCATAC | cDNA Primer |
| 43 | MM2239 | CCGTCTGTCCAGACTATGCA | cDNA Primer |
| 44 | MM2240 | CCGTCTGTCCAGACTGTACA | cDNA Primer |
| 45 | MM2255 | CCGTCTGTCCAGACTGTACAA | cDNA Primer |
| 46 | MM2242 | CCGTCTGTCCAGACAGCAC | cDNA Primer |
| 55 | MM2241 | CCGTCTGTCCAGATTGTACAA | cDNA primer |

Real-Time PCR Amplification

Amplification from the short RNA target sequence of only 22 bp was accomplished by first performing cDNA reaction with a bi-partite primer. The first portion of the cDNA primers was complementary to the 3' portion of the target miRNA sequences. The second portion of the cDNA primers contained 5' target-independent tail sequence that increased the overall primer $T_m$ to allow PCR amplification at an annealing temperature of approximately 55° C. Similarly, the forward primer was bi-partite with a 3'-end containing target specific sequences and a 5' extension that increased overall primer $T_m$ to allow standard PCR following extension from a primer initially hybridized at a lower temperature.

PCR reaction mix conditions were as follows: 25 µL reactions in 1× ISOlution buffer (EraGen, Madison, Wis.), 1× Titanium Taq DNA polymerase (Clontech, CA) at manufacturer's recommended concentration, and 0.5 Units/µL Maloney Murine Leukemia Virus reverse transcriptase. PCR primers were used at concentration of 200 nM.

Cycling parameters on ABI Prism 7700 (ABI, Foster City, Calif.) real-time thermal cycler for one-step reverse transcription polymerase chain reactions (RT-PCR) were:
1. 10 minutes @ 20° C., 5 minutes @ 37° C., 2 minutes @ 95° C., 1 cycle of 15 seconds (95° C., 60 seconds (40° C., 40 cycles of 15 seconds @ 95° C., 30 seconds @ 55° C. with optical read.
2. 15 minutes @ 37° C., 2 minutes @ 95° C., 1 cycle of 15 seconds @ 95° C., 60 seconds @ 40° C., 40 cycles of 15 seconds @ 95° C., 30 seconds @ 55° C. with optical read.
3. 15 minutes @ 42° C., 2 minutes @ 95° C., 1 cycle of 15 seconds @ 95° C., 60 seconds @ 40° C., 40 cycles of 15 seconds @ 95° C., 30 seconds @ 55° C. with optical read.

4. 15 minutes @ 50° C., 2 minutes @ 95° C., 1 cycle of 15 seconds @ 95° C., 60 seconds @ 40° C., 40 cycles of 15 seconds @ 95° C., 30 seconds @ 55° C. with optical read.

A thermal melt of 5 minutes duration from 60° C. to 95° C. with optical read was performed directly following the last step of thermal cycling for all conditions.

Instrument fluorescence data were exported as multicomponent files from the Applied Biosystems 7700 SDS software (Version 1.9) and then analyzed with MultiCode-RTx Analysis Software (EraGen Biosciences, Inc., Madison, Wis.). The MultiCode-RTx Analysis Software imports data from real-time instruments, determines signal decrease during the amplification and signal change during the melt and then performs cycle threshold and melt curve analyses.

Discrimination by cDNA Primer

Figure 2:
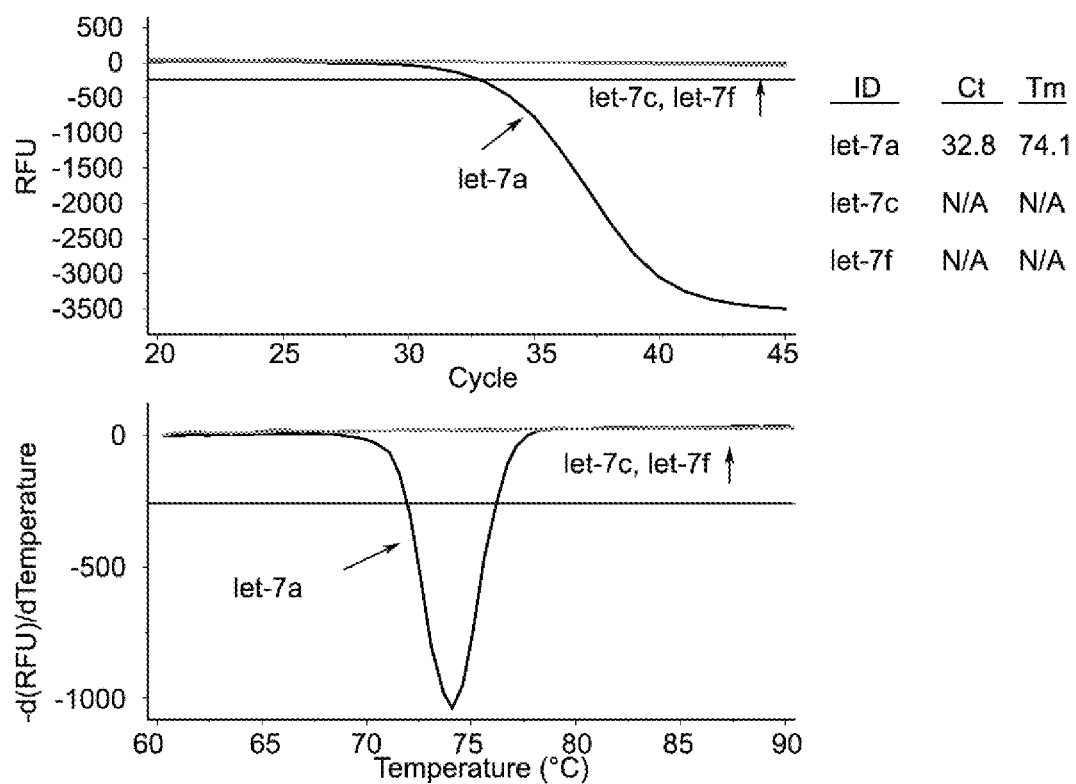
FIG. 2 shows graphs of the amplification and melt curves of the detection of miRNA using a cDNA primer designed to amplify let-7a, but not the let-7c or let-7f miRNA isoforms.

In the example shown in FIG. 2, a cDNA primer (SEQ ID NO:32) was designed to reverse transcribe and amplify the let-7a (SEQ ID NO: 1) species, but not the let-7c and let-7f (SEQ ID NOS:2, 3) species. SEQ ID NO: 32 was used in conjunction with a forward primer (SEQ ID NO: 11) designed to amplify all the let-7 species. Approximately 300,000 copies of synthetic miRNA were subjected to RT-PCR amplification. Amplification was only detected from the let-7a RNA.

Figure 3:
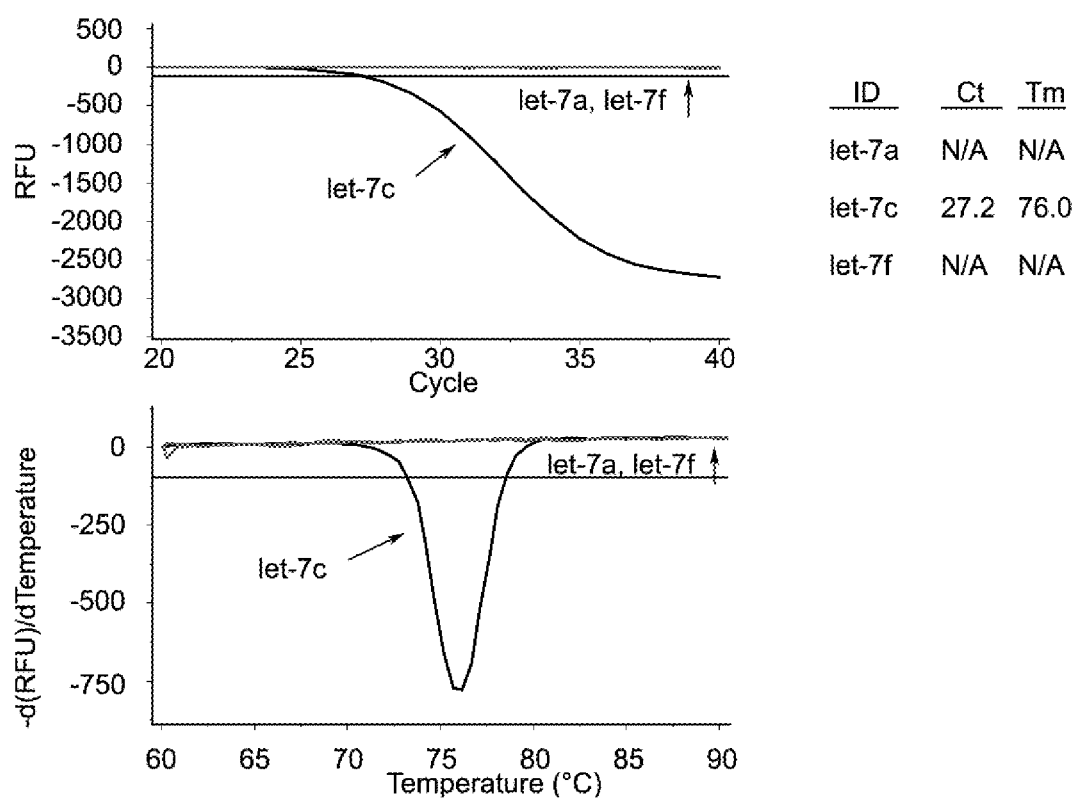
FIG. 3 shows graphs of the amplification and melt curves of the detection of miRNA using a cDNA primer designed to amplify let-7c, but not the let-7a or let-7f miRNA isoforms.

In the example shown in FIG. 3 a cDNA primer (SEQ ID NO:42) was designed to reverse transcribe and amplify only the let-7c (SEQ ID NO:2) species, but not the let-7a and let-7f (SEQ ID NOS: 1, 3) species. SEQ ID NO: 42 was used in conjunction with a forward primer (SEQ ID NO:6) designed to amplify all let-7 species. Approximately 300,000 copies of synthetic miRNA were subjected to RT-PCR amplification. Amplification was only detected from the let-7c RNA with a $C_T$ of 27.2 cycles.

Discrimination by Forward Primer

Figure 4:
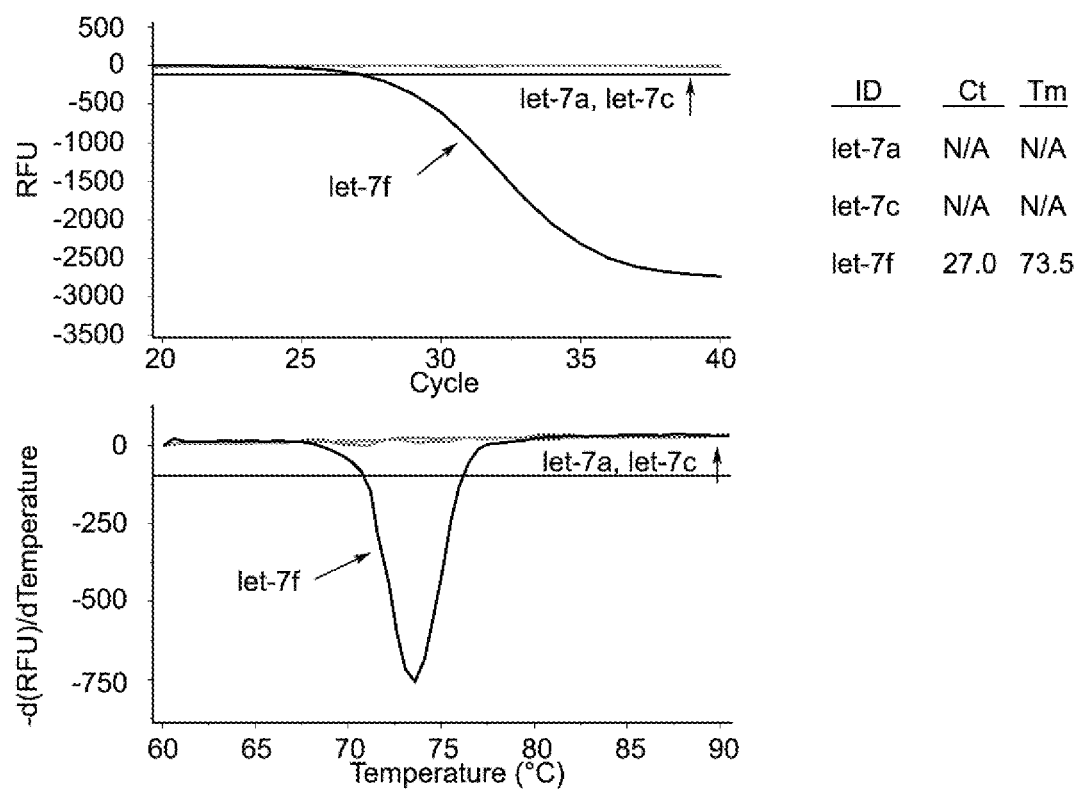
FIG. 4 shows graphs of the amplification and melt curves of the detection of miRNA using a cDNA primer designed to amplify let-7a-f isoforms and a forward primer designed to amplify only the let-7f miRNA isoform.

In the example shown in FIG. 4, a cDNA primer (SEQ ID NO:30) was designed to reverse transcribe and amplify the let-7a-f (SEQ ID NOS: 1, 2, 3) species. This primer was used in conjunction with a forward primer (SEQ ID NO: 16) designed to amplify only the let-7f species (SEQ ID NO:3). Approximately 300,000 copies of synthetic miRNA were subjected to RT-PCR amplification. Amplification was detected from only the let-7f RNA with a cycle threshold of 27.0 cycles.

Discrimination by Thermal Melt

Figure 5:
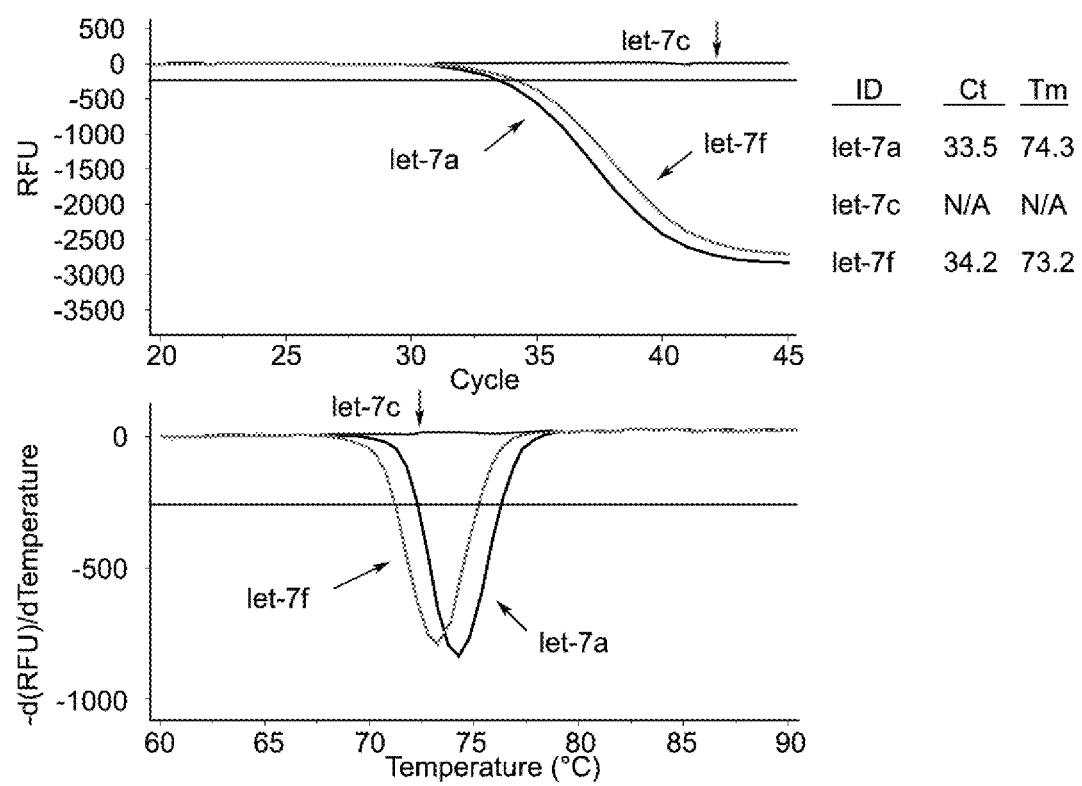
FIG. 5 shows graphs of the amplification and melt curves of the detection of miRNA using a cDNA primer designed to amplify let-7a and let-7f isoforms and a forward primer designed to amplify all let-7 miRNA isoforms. The amplification products were detected by a difference in $T_m$ during the melt curve analysis.

In the example shown in FIG. 5, a cDNA primer (SEQ ID NO:32) designed to reverse transcribe and amplify the let-7a and let-7f species, but not the let-7c species, was used in conjunction with a forward primer (SEQ ID NO:6) designed to amplify all the let-7 species. Approximately 300,000 copies of synthetic miRNA (SEQ ID NOS: 1, 2, 3) were RT-PCR amplified. No amplification was detected from the let-7c RNA, but both the let-7a and let-7f RNA were detected. In addition, the thermal melting temperature ($T_m$) of the let-7a and let-7f amplification products was determined to be 74.3° C. and 73.2° C. respectively. The 1.1° C. difference observed between the two species $T_m$ is expected, since let-7a (SEQ ID NO: 1) contains a guanine for adenine substitution as compared to let-7f (SEQ ID NO:3).

Relative Discrimination by Fluorescence Channel

Figure 6A:
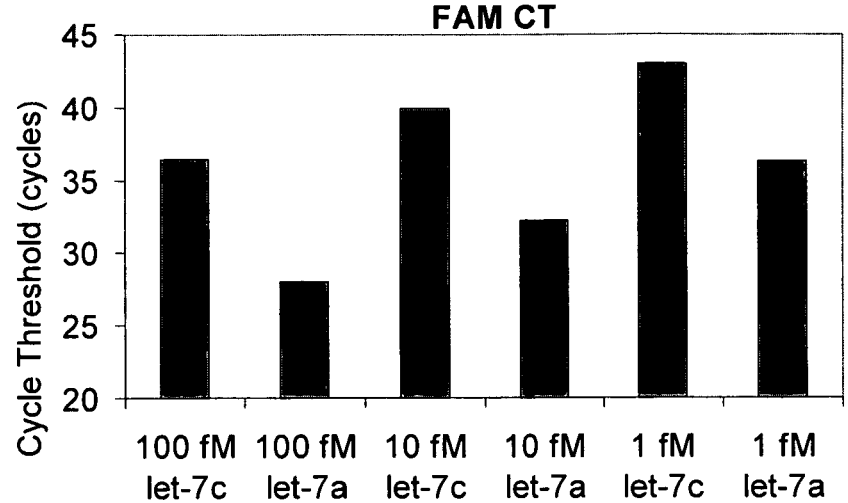
FIGS. 6A, 6B, and 6C charts show the results of detecting multiple miRNA isoforms simultaneously using differently labeled cDNA primers. Two competing cDNA primers of differing let-7 specificity were used in the assay.
Figure 6B:
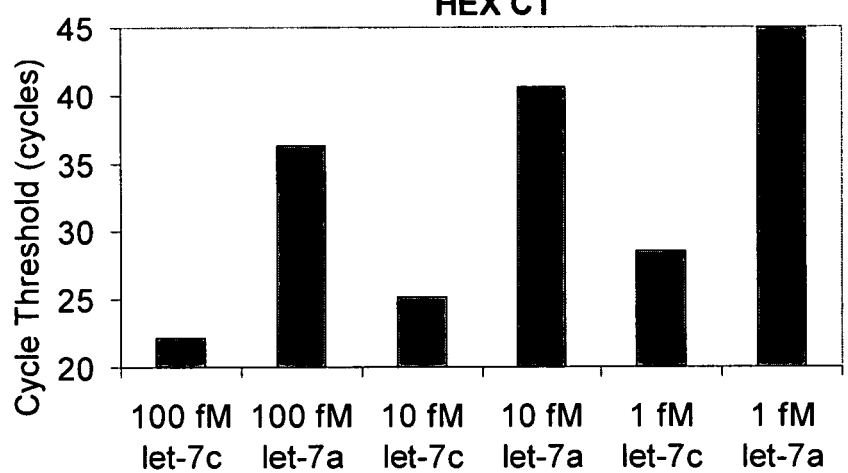
Figure 6C:
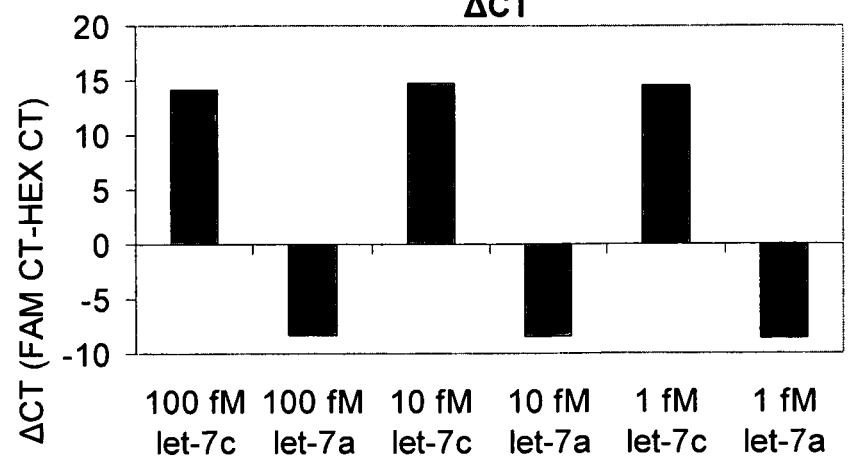

In the example shown in FIG. 6, two competing cDNA primers of differing let-7 specificity (SEQ ID NOS:24, 41) were labeled with distinguishable fluorophores FAM and HEX and used in conjunction with a forward primer (SEQ ID NO: 10) designed to amplify the let-7a-d species. Approximately 100 fM (300,000 copies), 10 fM (30,000 copies) and 1 fM (3,000 copies) of two synthetic let-7 miRNAs (SEQ ID 1, 2) were RT-PCR amplified. Amplification was detected from both fluorescent labels from the let-7a and let-7c RNA species. The observed cycle threshold ($C_T$) values were dependent on input concentration. Analysis of the difference in $C_T$ between the two channels (delta $C_T$ or $\Delta C_T$) indicates that $\Delta C_T$ does not depend on concentration. Thus, the relative concentration of let-7 species in a sample may be determined independent of the input target concentration.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member, any subgroup of members of the Markush group or other group, or the totality of members of the Markush group or other group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 nucleotides refers to groups having 1, 2, or 3 nucleotides. Similarly, a group having 1-5 nucleotides refers to groups having 1, 2, 3, 4, or 5 nucleotides, and so forth.

What is claimed is:

1. A method comprising:
   (a) contacting a sample to be tested for the presence or absence of a target small RNA with:
      (i) a linear first primer comprising a target binding region and a tail region, wherein the target binding region comprises about 12 or fewer nucleotides that are complementary to the small RNA;
      (ii) a linear second primer comprising a target binding region and a tail region, wherein the target binding region comprises about 12 or fewer nucleotides that are complementary to the reverse complement of the small RNA,
   wherein the tail regions of the first primer, the second primer, or both the first primer and the second primer comprise a first label and a first non-natural base;
   (b) extending the first primer under conditions suitable to produce a first reaction product of the small RNA, if present in the sample;
   (c) amplifying the first reaction product with the first primer and the second primer under conditions suitable to produce an amplification product, wherein a second non-natural base conjugated to a second label is incorporated into the amplification product opposite the first non-natural base, and wherein the first non-natural base is iso-C or iso-G and the second non-natural base is the other of iso-C or iso-G; and
   (d) detecting the amplification products produced in step (c) by observing a signal from the first label, the second label, or both the first label and the second label to determine the presence or absence of the target small RNA in the sample.

2. The method of claim 1, wherein the target small RNA is from about 16 to about 30 nucleotides in length.

3. The method of claim 1, wherein the target binding regions of the first primer and the second primer are each from about 7 to about 10 nucleotides in length.

4. The method of claim 1, wherein the tail regions of the first primer and the second primer are each from about 10 to about 25 nucleotides in length.

5. The method of claim 1, wherein the tail region of the first primer, the second primer, or both comprises at least two non-natural bases.

6. The method of claim 1, wherein the tail region of the both primers comprise at least one non-natural base.

7. The method of claim 1, wherein the first non-natural base is iso-C and the second non-natural base is iso-G.

8. The method of claim 1, wherein the step of extending is performed at a temperature from about 15° C. to about 50° C.

9. The method of claim 1, wherein the step of amplifying comprises a first annealing step performed at a temperature from about 35° C. to about 45° C.

10. The method of claim 9, wherein the step of amplifying comprises subsequent annealing steps performed at a temperature at least about 55° C.

11. The method of claim 1, wherein the first primer, the second primer, or both are capable of amplifying multiple related small RNA isoforms.

12. The method of claim 1, wherein the first primer, the second primer, or both are specific for a single small RNA isoform.

13. The method of claim 12, wherein the single small RNA isoform differs from other isoforms at one or more specific nucleotide positions, and at least the 4 terminal nucleotides at the 3' end of first primer, the second primer, or both are complementary to the single isoform, but not complementary to the other isoforms.

14. The method of claim 1, wherein the labels are fluorophores.

15. The method of claim 1, wherein the first label is a fluorophore and the second label is a quencher.

16. The method of claim 1, wherein the step of detecting comprises quantifying the amount of the small RNA in the sample.

17. The method of claim 16, wherein quantifying comprises correlating the amount of signal observed from the first label, the second label or both the first label and the second label, to the amount of small RNA in the sample.

18. The method of claim 1, wherein the step of detecting comprises determining the melting temperature of the amplification products.

19. A method comprising:
   (a) contacting a sample to be tested for the presence or absence of at least two target small RNA isoforms with:
      (i) a linear first primer comprising a target binding region and a tail region, wherein the target binding region comprises about 12 or fewer nucleotides that are complementary to at least two small RNA isoforms;
      (ii) a linear second primer comprising a target binding region and a tail region, wherein the target binding region comprises about 12 or fewer nucleotides that are complementary to the reverse complement of a first small RNA isoform, and the tail region comprises a first label and a first non-natural base;
      (iii) a linear third primer comprising a target binding region and a tail region, wherein the target binding region comprises about 12 or fewer nucleotides that are complementary to the reverse complement of a second small RNA isoform, and the tail region comprises a second label and a second occurrence of the first non-natural base;
   (b) extending the first primer under conditions suitable to produce a first reaction product of the at least two small RNA isoforms, if present in the sample;
   (c) amplifying the first reaction product, with the first primer, the second primer, and the third primer under conditions suitable to produce amplification products of the first small RNA isoform and the second small RNA isoform, wherein a second non-natural base comprising a third label is incorporated into the amplification products opposite the first non-natural base and wherein the first non-natural base is iso-C or iso-G, and the second non-natural base is the other of iso-C or iso-G; and;
   (d) detecting the amplification products produced in step (c) by observing a signal from the first label, the second label, or both the first label and the second label, to determine the presence or absence of the target small RNA isoforms in the sample.

* * * * *